(12) United States Patent
Koob

(10) Patent No.: US 10,689,621 B2
(45) Date of Patent: Jun. 23, 2020

(54) KITS AND MATERIALS FOR IMPLANTABLE COLLAGEN DEVICES

(71) Applicant: MiMedx Group, Inc., Marietta, GA (US)

(72) Inventor: Thomas J. Koob, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 343 days.

(21) Appl. No.: 15/843,695

(22) Filed: Dec. 15, 2017

(65) Prior Publication Data

US 2018/0127711 A1    May 10, 2018

Related U.S. Application Data

(60) Continuation of application No. 14/618,310, filed on Feb. 10, 2015, now Pat. No. 9,873,861, which is a
(Continued)

(51) Int. Cl.
*C12N 5/077* (2010.01)
*A61F 2/02* (2006.01)
(Continued)

(52) U.S. Cl.
CPC ............ *C12N 5/066* (2013.01); *A61F 2/0095* (2013.01); *A61F 2/02* (2013.01); *A61F 2/08* (2013.01); *A61L 27/24* (2013.01); *A61L 27/3804* (2013.01); *A61L 27/386* (2013.01); *A61L 2430/10* (2013.01); *C12N 2506/1307* (2013.01);
(Continued)

(58) Field of Classification Search
CPC ........ A61F 2/0805; A61F 2/08; A61F 2/0811; A61F 2/02; A61F 2/0095; A61B 5/4523; A61B 5/4533; C12N 5/066
See application file for complete search history.

(56) References Cited

U.S. PATENT DOCUMENTS

| 3,316,699 A | 5/1967 | Mattingly |
| 4,590,928 A | 5/1986 | Hunt et al. |

(Continued)

FOREIGN PATENT DOCUMENTS

| CA | 2 285 161 A1 | 4/2001 |
| EP | 1 319 415 A1 | 6/2003 |

(Continued)

OTHER PUBLICATIONS

Altman et al. "Cell differentiation be mechanical stress" *The FASEB Journal* 16:270-272 (2002).
(Continued)

*Primary Examiner* — Jason-Dennis N Stewart
(74) *Attorney, Agent, or Firm* — Myers Bigel, P.A.

(57) ABSTRACT

The invention relates to implantable collagen devices made by seeding at least one elongate collagen construct, e.g., comprising at least one elongate synthetic collagen fiber with a plurality of cells and applying a strain and/or stress to the at least one elongate collagen fiber to induce the cells to differentiate into target phenotypes, e.g., tendon or ligament phenotype cells (and/or fibroblasts), typically with an extracellular matrix of collagen to organize into a tissue on the at least one collagen fiber.

11 Claims, 13 Drawing Sheets

Related U.S. Application Data division of application No. 13/667,507, filed on Nov. 2, 2012, now Pat. No. 8,986,378.

(60) Provisional application No. 61/554,645, filed on Nov. 2, 2011.

(51) Int. Cl.
  A61F 2/00    (2006.01)
  A61L 27/24   (2006.01)
  A61L 27/38   (2006.01)
  A61F 2/08    (2006.01)

(52) U.S. Cl.
  CPC .. *C12N 2506/1346* (2013.01); *C12N 2527/00* (2013.01); *C12N 2533/54* (2013.01)

(56) References Cited

U.S. PATENT DOCUMENTS

| | | |
|---|---|---|
| 4,792,336 A | 12/1988 | Hlavacek et al. |
| 4,841,962 A | 6/1989 | Berg et al. |
| 4,883,486 A | 11/1989 | Kapadia et al. |
| 4,979,956 A | 12/1990 | Silvestrini |
| 5,078,744 A | 1/1992 | Chvapil |
| 5,106,949 A | 4/1992 | Kemp et al. |
| 5,256,418 A | 10/1993 | Kemp et al. |
| 5,263,984 A | 11/1993 | Li et al. |
| 5,266,480 A | 11/1993 | Naughton et al. |
| 5,378,469 A | 1/1995 | Kemp et al. |
| 5,656,605 A | 8/1997 | Hansson et al. |
| 5,713,374 A | 2/1998 | Pachence et al. |
| 5,718,012 A | 2/1998 | Cavallaro |
| 5,718,717 A | 2/1998 | Bonutti |
| 5,770,417 A | 6/1998 | Vacanti et al. |
| 5,855,619 A | 1/1999 | Caplan et al. |
| 5,931,165 A * | 8/1999 | Reich ............. A61B 17/00491 128/898 |
| 6,090,117 A | 7/2000 | Shimizu |
| 6,224,630 B1 | 5/2001 | Bao et al. |
| 6,277,397 B1 | 8/2001 | Shimizu |
| 6,280,474 B1 | 8/2001 | Cassidy et al. |
| 6,292,697 B1 | 9/2001 | Roberts |
| 6,335,007 B1 | 1/2002 | Shimizu et al. |
| 6,531,147 B2 | 3/2003 | Sawhney et al. |
| 6,537,567 B1 | 3/2003 | Niklason et al. |
| 6,565,960 B2 | 5/2003 | Koob et al. |
| 6,589,257 B1 | 7/2003 | Shimizu |
| 6,592,623 B1 | 7/2003 | Bowlin |
| 6,645,247 B2 | 11/2003 | Ferree |
| 6,692,528 B2 | 2/2004 | Ward et al. |
| 6,713,537 B1 | 3/2004 | Ueda et al. |
| 6,730,124 B2 | 5/2004 | Steiner |
| 6,752,831 B2 | 6/2004 | Sybert et al. |
| 6,821,530 B2 | 11/2004 | Koob et al. |
| 6,936,072 B2 | 8/2005 | Lambrecht et al. |
| 6,955,683 B2 | 10/2005 | Bonutti |
| 6,962,814 B2 | 11/2005 | Mitchell et al. |
| 7,084,082 B1 | 8/2006 | Shimizu |
| 7,090,690 B2 | 8/2006 | Foerster et al. |
| 7,115,146 B2 | 10/2006 | Boyer et al. |
| 7,135,040 B2 | 11/2006 | Wang et al. |
| 7,309,359 B2 | 12/2007 | Trieu et al. |
| 7,354,627 B2 | 4/2008 | Pedrozo et al. |
| 7,901,455 B2 | 3/2011 | Koob et al. |
| 2001/0018619 A1 | 8/2001 | Enzerink et al. |
| 2002/0037940 A1 | 3/2002 | Koob et al. |
| 2002/0123805 A1 | 8/2002 | Murray et al. |
| 2003/0100108 A1 | 5/2003 | Altman et al. |
| 2003/0230316 A1 | 12/2003 | Glucksman et al. |
| 2004/0110439 A1 | 6/2004 | Chaikof et al. |
| 2004/0131562 A1 | 7/2004 | Gower et al. |
| 2004/0193241 A1 | 9/2004 | Stinson |
| 2004/0224406 A1 | 11/2004 | Altman et al. |
| 2004/0267362 A1 | 12/2004 | Hwang et al. |
| 2006/0095134 A1 | 5/2006 | Trieu et al. |
| 2006/0257377 A1 | 11/2006 | Atala et al. |
| 2006/0263417 A1 | 11/2006 | Lelkes et al. |
| 2007/0118217 A1 | 5/2007 | Brulez et al. |
| 2007/0134305 A1 | 6/2007 | Zilberman |
| 2007/0248643 A1 | 10/2007 | Devore et al. |
| 2008/0020012 A1 | 1/2008 | Ju et al. |
| 2008/0038352 A1 | 2/2008 | Simpson et al. |
| 2008/0124371 A1 | 5/2008 | Turos et al. |
| 2008/0161917 A1 | 7/2008 | Koob et al. |
| 2008/0188933 A1 | 8/2008 | Koob et al. |
| 2008/0200992 A1 | 8/2008 | Koob et al. |
| 2008/0215150 A1 | 9/2008 | Koob et al. |
| 2009/0216233 A1 | 8/2009 | Wiedrich et al. |
| 2009/0287308 A1 | 11/2009 | Davis et al. |
| 2010/0094318 A1 | 4/2010 | Li et al. |
| 2010/0094404 A1 | 4/2010 | Greenhalgh et al. |
| 2010/0144007 A1 | 6/2010 | Bryant et al. |
| 2011/0189773 A1 | 8/2011 | Altman et al. |
| 2011/0282448 A1 | 11/2011 | Paulos |

FOREIGN PATENT DOCUMENTS

| | | |
|---|---|---|
| EP | 1 493 404 A1 | 1/2005 |
| WO | WO 96/14095 A1 | 5/1996 |
| WO | WO 01/15754 A1 | 3/2001 |
| WO | WO 01/72241 A1 | 10/2001 |
| WO | WO 2008/041183 A2 | 4/2008 |
| WO | WO 2012/003465 A2 | 1/2012 |
| WO | WO 2012/121986 A2 | 9/2012 |

OTHER PUBLICATIONS

Becker et al. "Early active motion following a beveled technique of flexor tendon repair: Report on fifty cases" *Journal of Hand Surgery* 1979, vol. 4 No. 5, pp. 454-460.

Biosingularity, Advances in biological systems, Google Ad, MIT Technology Review, 2006, 1 Page.

Breshears et al. "The Effect of Uniaxial Cyclic Tensile Load on Gene Expression in Canine Cranial Cruciate Ligamentocytes" *Veterinary Surgery* 2010, pp. 433-443, vol. 39.

Brunelli et al. "Slip-knot flexor tendon suture in zone II allowing immediate mobilisation" *The Hand* 1983, vol. 15, pp. 352-358.

Chen et al. "Biodegradable hybrid scaffolds for tissue engineering" *Proceeding of Intelligent Material Symposium* [in Japanese], 2001, pp. 70-71, vol. 11.

Chen et al. "Preparation of Biodegradable Hybrid Sponge and Its Application to Three-dimensional Chondrocyte Cultures" *The Japanese Journal of Artificial Organs* 2000, pp. 463-467, vol. 29, No. 2.

Flexcell International Corporation, company information, http://www.flexcellint.com/about.htm © 2011, 2 pages, printed from the internet Sep. 12, 2011.

Garvin et al. "Novel System for Engineering Bioartificial Tendons and Application of Mechanical Load" *Tissue Engineering* 2003, pp. 967-979, vol. 9, No. 5.

Greis et al. "The influence of tendon length and fit on the strength of the tendon-bone tunnel complex" *Am. J. Sports Med.* 2001, 29:493-497.

Grog "The Reef (Square) Knot" Animated Knots by Grog, downloaded at http://www.animatedknots.com/reef/index.php, on May 28, 2009 using WayBack Machine on www.archive.org for publication date of Dec. 26, 2005.

Integra™ NeuraGen™ Nerve Guide *Product Brochure* 4 pages (2005).

Integra™ NeuraGen™ Nerve Guide, Product Webpage, http://www.integra-ls.com/products/?product=88, Date unknown but believed to be prior to the filing date of the present application, 2 pages.

Integra™ NeuraWrap™ Nerve Protector, Product Webpage, http://www.integra-ls.com/products/?product=198, Date unknown but believed to be prior to the filing date of the present application, 2 pages.

International Search Report and Written Opinion for corresponding PCT Application No. PCT/US2012/063229, dated Feb. 26, 2013.

Kakisis et al. "Artificial blood vessel: The Holy Grail of peripheral vascular surgery" *Journal of Vascular Surgery* vol. 41, Issue 2, 2003, pp. 349-354 (abstract only).

(56) References Cited

OTHER PUBLICATIONS

Kanematsu et al. "Collagenous matrices as released carriers of exogenous growth factors" *Biomaterials* 2004, pp. 4513-4520, vol. 25.

Khan et al. "Mechanotherapy: how physical therapists' prescription of exercise promotes tissue repair" *Journal of Sports Medicine* 2009, pp. 247-251, vol. 43.

Koob et al. "Biocompatibility of NDGA-polymerized collagen fibers. I. Evaluation of cytotoxicity with tendon fibroblasts in vitro" © 2001 John Wiley & Sons, Inc.

Koob et al. "Biocompatibility of NDGA-polymerized collagen fibers. II. Attachment, proliferation, and migration of tendon fibroblasts in vitro" © 2001 John Wiley & Sons, Inc.

Koob et al. "Compression Loading in Vitro Regulates Proteoglycan Synthesis by Tendon Firbrocartilage" *Archives of Biochemistry and Biophysics* Oct. 1992, pp. 303-312, vol. 298, No. 1.

Koob et al. "Material properties of polymerized NDGA-collagen composite fibers: developmentt of biologically based tendon constructs" *Biomaterials* Jan. 2002, pp. 203-212, vol. 23, No. 1.

Koob et al. "Mechanical and thermal properties of novel polymerized NDGA-gelatin hydrogels" *Biomaterials* 2003, 1285-1292, vol. 24.

Koob, Thomas J., Biomimetic approaches to tendon repair, Comparative Biochemistry and Physiology Part A, 2002, pp. 1171-1192, vol. 133.

Martin et al. "Anterior Cruciate Ligament Graft Preparation: A New and Quick Alternative to the Whipstitch" *Arthroscopy: The Journal of Arthroscopic & Related Surgery* Online Publication Date of Nov. 29, 2006.

Messina "The double armed suture: Tendon repair with immediate mobilization of the fingers" *Journal of Hand Surgery* 1992, 17A:137-142.

Nottage et al., Arthoscopic Knot Tying Techniques, Arthroscopy: The Journal of Arthroscopic & Related Surgery 15(1999): 515-521.

Oberpenning et al. "De novo reconstitution of a functional mammalian urinary bladder by tissue engineering" *Nature Biotechnology* Feb. 1999, pp. 149-155, vol. 17.

Powell et al. "Forces transmitted along human flexor tendons during passive and active movements of the fingers" *J. Hand Surg.* 2004, 29:4:386-389.

Product advertisement, Conair QB3ECS Quick Braid Styling Kit, © 2007 (1 page).

Qiu et al. "Cyclic tension promotes fibroblastic differentiation of human MSCs cultured on collagen-fibre scaffolds" *Journal of Tissue Engineering and Regenerative Medicine* 10:989-999 (2016).

Rodeo et al. "Tendon healing in a bone tunnel. A biomechanical and histological study in a dog" *J. Bone Joint Surg.* 1993, 75:1795-1803.

Savage et al. "Flexor tendon repair using a "six strand" method of repair and early active mobilisation" *Journal of Hand Surgery* (British Volume,1989) 14B:396-399.

Silva et al. "The insertion site of the canine flexor digitorum profundus tendon heals slowly following injury and suture repair" *J. Orthop. Res.* 2002, 20:447-453.

Triantafillopoulos et al. "Nandrolone Decanoate and Load Increase Remodeling and Strength in Human Supraspinatus Bioartificial Tendons" *The American Journal of Sports Medicine* 2004, pp. 934-943, vol. 32, No. 4.

Trotter et al. "Molecular structure and functional morphology of echinoderm collagen fibrils" *Cell Tiss. Res.* 1994, 275: 451-458.

Wall et al. "Early responses to mechanical load in tendon: Role for calcium signaling, gap junctions and intercellular communication" *J. Musculoskelet Neuronal Interact* 2005, pp. 70-84, vol. 5, No. 1.

Wang "Mechanobiology of tendon" *Journal of Biomechanics* 39:1563-1582 (2006).

Young et al. "Use of Mesenchymal Stem Cells in a Collagen Matrix for Achilles Tendon Repair" *Journal of Orthopaedic Research* 16:406-413 (1998).

\* cited by examiner

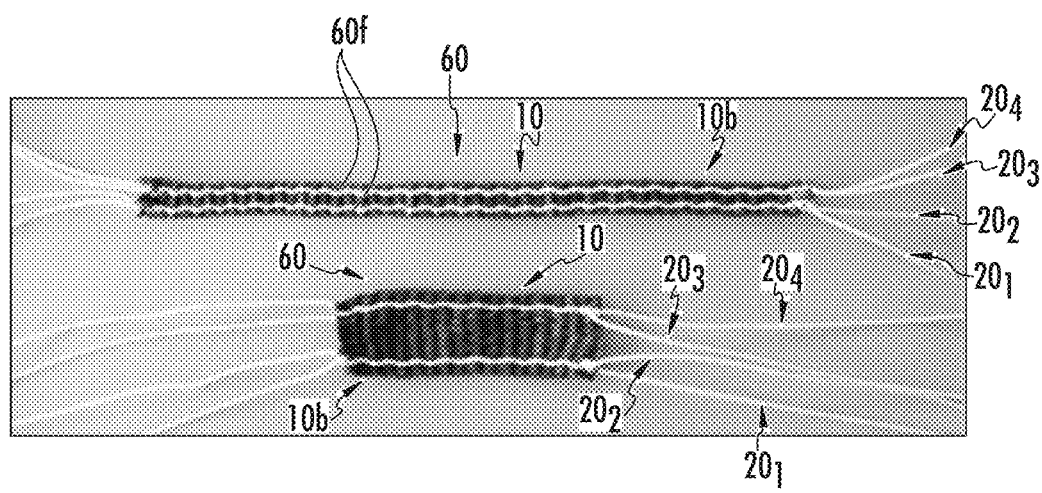
FIG. 3A
FIG. 3B
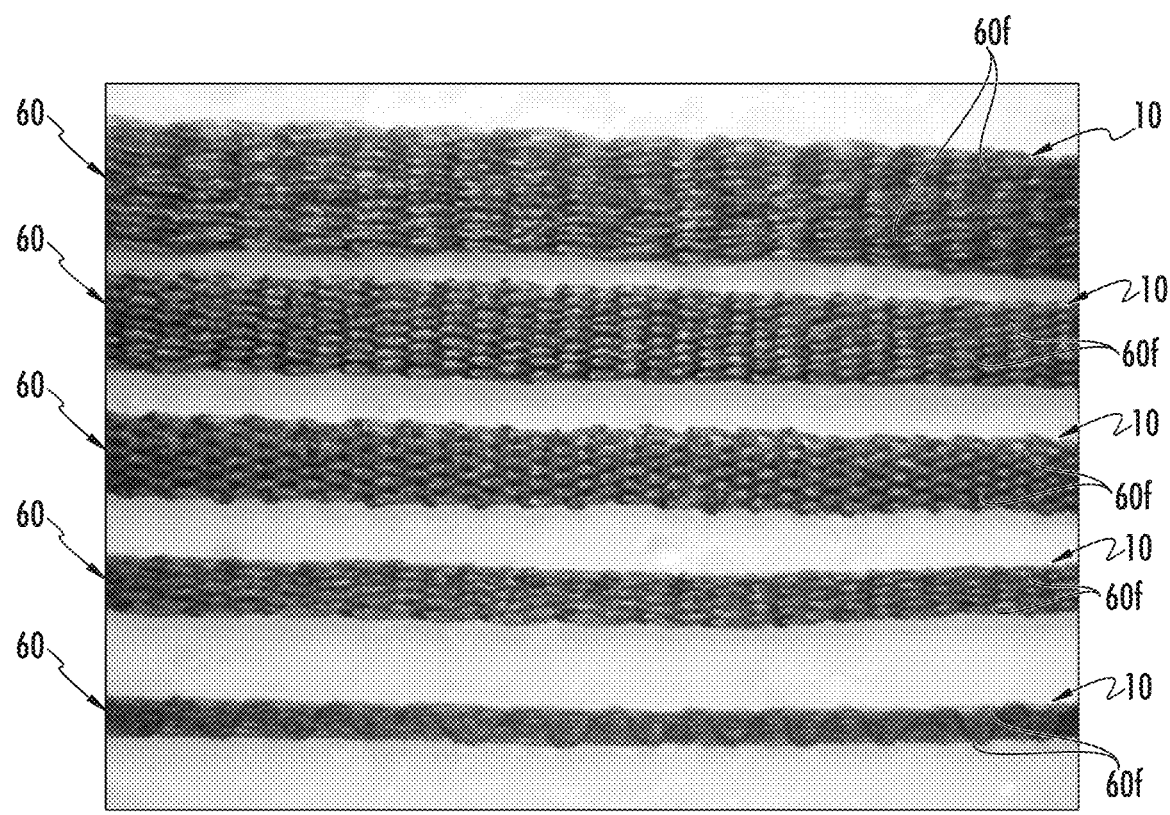
FIG. 3C

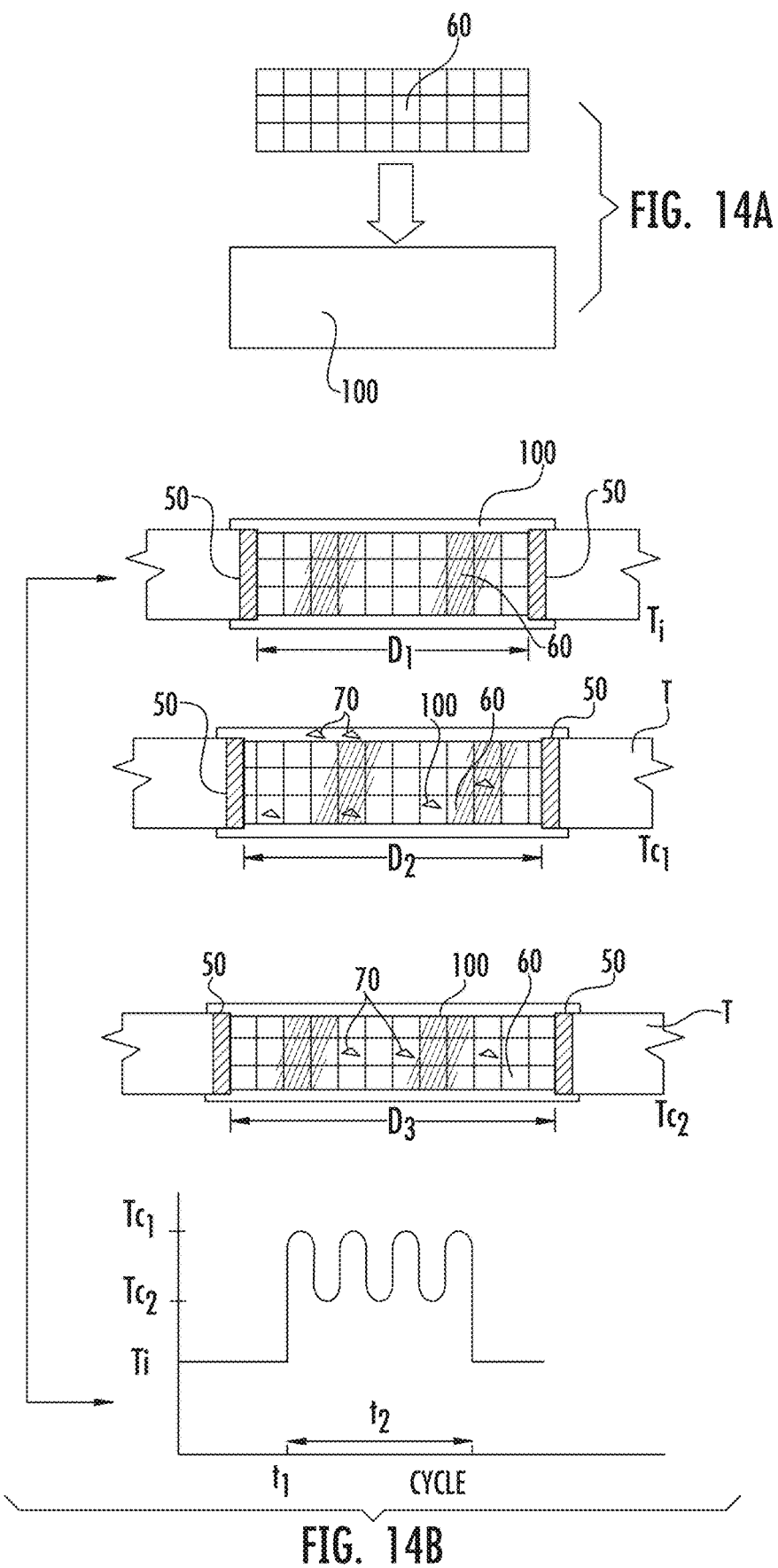

KITS AND MATERIALS FOR IMPLANTABLE COLLAGEN DEVICES

RELATED APPLICATIONS

This is a continuation application of U.S. patent application Ser. No. 14/618,310, filed Feb. 10, 2015, which is a divisional application of U.S. patent application Ser. No. 13/667,507, filed Nov. 2, 2012, now U.S. Pat. No. 8,986,378, issued Mar. 24, 2015, which claims the benefit of and priority to U.S. Provisional Patent Application Ser. No. 61/554,645, filed Nov. 2, 2011, the contents of which are hereby incorporated by reference as if recited in full herein.

FIELD OF THE INVENTION

The invention relates to implantable collagen fiber devices and methods of making the same.

BACKGROUND OF THE INVENTION

Surgical repair or replacement of injured or diseased tissues, such as tendons and ligaments, often relies on the use of autologous tissue. However, an injury resulting from the harvesting of the autologous tissue can result in cell morbidity at a donor site.

SUMMARY OF EMBODIMENTS OF THE INVENTION

Embodiments of the invention are directed to collagen-based materials, typically comprising elongate synthetic collagen fibers, with differentiated cells and/or an extracellular matrix of collagen.

A first aspect of the present invention is directed to implantable collagen fiber constructs. The constructs include a plurality of elongate collagen fibers and a plurality of cells attached to the elongate collagen fibers. The attached cells include tendon or ligament phenotype cells or the attached cells include tendon or ligament phenotype cells and an extracellular matrix that includes collagen. The collagen in the extracellular matrix is present in an amount greater than other extracellular matrix proteins.

The plurality of elongate collagen fibers can be arranged as construct body. The tendon or ligament phenotype cells and extracellular matrix that includes (predominantly) collagen can be organized into tendon-like or ligament-like tissue that increases a volume of the construct body, measured dry, by between about 20-200% or that increases a thickness of the construct body by between 10%-200%.

The plurality of elongate collagen fibers can be arranged as a construct body. The tendon or ligament phenotype cells and extracellular matrix of collagen can extend over at least 50% of a length of the construct body shape about the elongate collagen fibers.

The fibers can include tendon phenotype cells and at least 20% extracellular matrix of collagen by volume, dry.

The plurality of elongate collagen fibers define a construct body with a shape and the attached cells includes the tendon or ligament phenotype cells and the extracellular matrix of collagen, in an amount between about 20% to 200% by volume of the construct body, dry.

The collagen fibers can be cross-linked with NDGA and the attached tendon or ligament phenotype cells extend over at least a major portion of a surface area of each collagen fiber for at least 50% of an overall length of the collagen fibers.

The plurality of collagen fibers can be wound, twisted, braided and/or woven together.

The implantable collagen fiber construct can be a tendon or a ligament prosthesis and the collagen fiber construct can have a tensile strength, stiffness, and dynamic flexibility that meets or exceeds that of a natural tissue the collagen construct is designed to mimic.

The attached cells are differentiated cells derived from cells selected from the group consisting of embryonic, neonatal or adult cells, pluripotent stem cells from any tissue source, mesenchymal stem cells, tendon and/or ligament fibroblasts, or combinations thereof.

The plurality of elongate collagen fibers can be arranged in a construct body shape, and the cells can be organized into tendon-like or ligament-like tissue that increases a thickness of the construct body between 100%-200%.

Other aspects are directed to methods of processing an implantable collagen fiber(s). The methods include: (a) placing at least one elongate collagen fiber in a desired orientation in a tissue culture vessel; (b) seeding the at least one elongate collagen fiber with a plurality of cells while in the vessel; and (c) automatically applying a strain and/or stress to the at least one elongate collagen fiber in the vessel to cause at least one of the following cellular actions: (i) induce the cells to differentiate into tendon or ligament fibroblasts or tendon or ligament phenotype cells; (ii) form an extracellular matrix of some or at least a major portion of collagen; or (iii) both induce the cells to differentiate into tendon or ligament fibroblasts or tendon or ligament phenotype cells and form an extracellular matrix, wherein the extracellular matrix comprises collagen in amount greater than other proteins.

The method can also include (d) producing an implantable collagen fiber construct with (i) the tendon or ligament phenotype differentiated cells or (ii) the tendon or ligament phenotype differentiated cells and the collagen based extracellular matrix based, at least in part, on the applying step.

The tissue culture vessel can include a flexible pouch that holds the at least one collagen fiber in the desired orientation during the applying step.

The seeding step can be carried out by introducing a fluid comprising the plurality of cells into the pouch via a fluid port of the flexible pouch.

The cells of the seeding step can be selected from the group consisting of embryonic, neonatal or adult cells, pluripotent stem cells from any tissue source, mesenchymal stem cells, tendon and/or ligament fibroblasts, or combinations thereof.

The seeding step can be carried by immersing or submerging the at least one elongate collagen fiber into a fluid contained in the flexible pouch. The fluid comprises the plurality of cells (typically as a cell solution or suspension).

The applying step can be carried out by attaching a translating mechanical tensioner to opposing end portions of the flexible pouch.

The applying step can be carried out at least periodically after seeding.

The applying step can be carried out after a time sufficient to allow seed attachment to the at least one fiber, then at least periodically until implantation.

The applying step can be carried out to first apply a static strain or stress, then apply a cyclic strain or stress.

The applying step can be carried out to apply a static initial offset strain to the at least one elongate collagen fiber after the seeding step, then after a sufficient number of cells attach to the at least one fiber and cell proliferation on the at least one collagen fiber to a desired level, the applying step applies a cyclical strain and/or stress.

The static strain can be carried out after cells introduced by the seeding step attach to the at least one elongate collagen fiber in a desired amount for a first time period, then the cyclic strain and/or stress is applied for between 5 minutes/day to 24 hours/day for a subsequent time period.

The method can include, prior to the placing step, winding, twisting, braiding or weaving a plurality of the elongate collagen fibers into a collagen fiber construct at a defined tension $t_f$. The applying step can hold opposing end portions of the collagen fiber construct in the pouch at the tension $t_f$.

The applying step, at least initially, can include applying a first low strain and/or tensile load to the collagen fiber construct, then applying cyclic strain or tension that varies between 2% to about 15% above the first low strain or tensile load.

The cycling the tensile load and/or strain can be carried out after the seeding step.

The cyclic strain can be applied to the at least one elongate collagen fiber for between about 5 minutes to about 24 hours per day for a defined number of days and/or until the cells differentiate sufficiently and/or produce a desired amount of the extracellular matrix of collagen on the at least one collagen fiber.

The cyclic strain can vary between about 2% to about 10% above the initial strain and cycles at between about 0.5 Hz to about 3 Hz for a defined time period of at least 30 minutes every 24 hours.

The strain and/or stress can be uniaxial.

The at least one fiber can be a plurality of fibers arranged as an implantable collagen fiber construct. The construct can have a tensile strength, stiffness, and dynamic flexibility that meets or exceeds that of a natural tissue the implantable collagen fiber construct is designed to mimic.

The tissue can be a tendon or a ligament prosthesis.

Other embodiments are directed to medical kits. The kits include a single-use flexible package holding a collagen construct comprising a plurality of elongate collagen fibers. The collagen fibers include ligament or tendon phenotype cells, and the tendon or ligament phenotype cells extend over at least 50% of a length of the collagen fibers.

The elongate collagen fibers of the construct can also include an extracellular matrix comprising collagen, with the collagen present in an amount greater than other extracellular matrix proteins.

The flexible package can include a polymeric pouch. The kit can include an autotensioner releasably attached to the package to apply a maintenance strain and/or stress to the tissue.

The collagen fibers can be cross-linked with NDGA and the tendon or ligament phenotype cells cover at least a major portion of a surface area of each of the collagen fibers for at least 50% of the length of the collagen fibers.

The plurality of elongate collagen fibers can be wound, braided, twisted and/or woven together.

The collagen construct can be a tendon or ligament prosthesis and has a tensile strength, stiffness, and dynamic flexibility that meets or exceeds that of a natural tissue the collagen construct is designed to mimic.

The cells can be differentiated cells derived from cells selected from the group consisting of embryonic, neonatal or adult cells, pluripotent stem cells, mesenchymal stem cells, tendon and/or ligament fibroblasts, or combinations thereof.

The plurality of collagen fibers can be between 2-1000 fibers.

Yet other embodiments are directed to medical materials that include at least one elongate synthetic collagen fiber with a plurality of cells attached to the elongate collagen fiber. The cells comprise defined phenotype cells or the cells comprise defined phenotype cells and an extracellular matrix comprising collagen, wherein collagen is present in an amount greater than other extracellular matrix proteins.

The at least one collagen fiber can include the defined phenotype cells and the extracellular matrix comprising collagen that increases a volume of the fiber, measured dry, by between about 20-200%.

The defined phenotype cells and extracellular matrix of collagen extend over at least 50% of a length and about at least a major portion of an outer surface of the at least one elongate collagen fiber.

The at least one collagen fiber includes the defined phenotype cells and at least 20% extracellular matrix of collagen by volume, dry.

The defined phenotype cells can be phenotype cells of natural (human or veterinary) tissue targeted for treatment using the at least one collagen fiber.

Other embodiments are directed to systems for mechanically applying strain and/or stress. The systems include: (a) a plurality of cooperating holding members adapted to attach to opposing end portions of a plurality of pouches enclosing respective collagen constructs; (b) at least one fluid source in fluid communication with the pouches, the at least one fluid source comprising a first fluid source with cells; and (c) at least one tensioner with an automated stroke cycle in communication with the holding members.

The system can also include a controller and user interface in communication with the tensioner. The user interface and controller can be configured to allow a user to select a cyclic stroke cycle of the tensioner to control stress/strain applied to the pouches.

The at least one fluid source can include a second fluid source in fluid communication with the pouches, the second fluid source comprising cell culture media devoid of cells.

The system can include an incubator with a housing that encloses the pouches, wherein the incubator can control one or more of a temperature, humidity, and/or gaseous atmosphere the pouches are exposed to in the incubator housing.

The system can include a flow control system in communication with the at least one fluid source and the controller. The controller can control operation of the flow control system to selectively direct when to flow fluid from the first fluid source to one or more of the pouches.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIGS. 3A and 3B are digital photographs of collagen constructs comprising ribbons with pairs of integrated sutures on each long side of the ribbon according to embodiments of the invention.

FIG. 3C is a digital photograph of collagen constructs comprising ribbons with no sutures according to embodiments of the invention.

FIG. 14A is a schematic illustration of a collagen fiber construct placed in a flexible package or bag/pouch according to embodiments of the present invention.

FIG. 14B is a schematic illustration of different loading configurations that can be used to apply a static and cyclic tensile loading, stress or strain with an associated exemplary timing diagram according to embodiments of the present invention.

DETAILED DESCRIPTION

Figure 1:
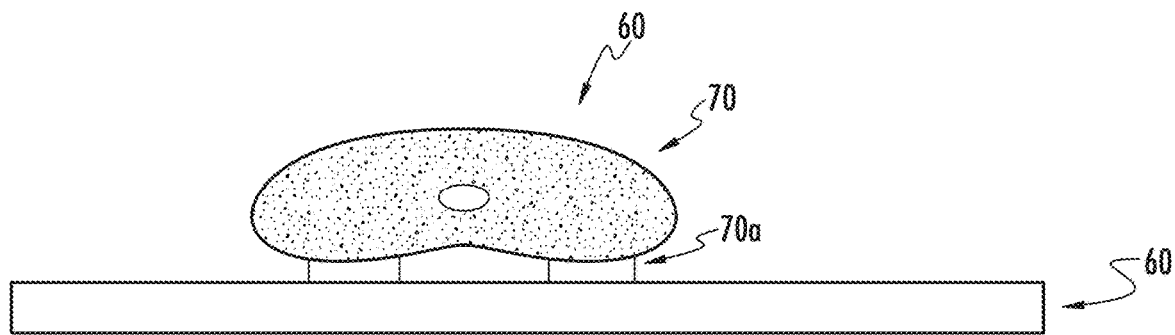
FIG. 1 is a schematic illustration of a cell attached to a collagen construct according to embodiments of the invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about," as used herein when referring to a measurable value such as an amount or concentration (e.g., the value of the strain and/or stress) and the like, is meant to encompass variations off 5% or less, such as 5%, 4%, 3%, 2%, 1%, 0.5%, or even 0.1% of the specified amount.

The term "sterile" means that the device or component meets or exceeds sterility guidelines for medical use.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity. The terminology used in the description of the invention herein is for the purpose of describing particular embodiments only and is not intended to be limiting of the invention. All publications, patent applications, patents and other references mentioned herein are incorporated by reference in their entirety.

Implantable Collagen Devices

The present invention is directed to implantable collagen devices comprising, consisting essentially of, or consisting of a collagen fiber construct and at least one cell, wherein the at least one cell is attached to the collagen fiber construct. Typically, the at least one cell is differentiated into a plurality of tendon and/or ligament phenotype cells.

The term "cell" as used herein refers to a cell from any source (e.g., human or animal; living or cadaveric) and can be an allogeneic cell (e.g., a cell from a source that is the same species as the subject/recipient of an implantable collagen device of the present invention), an autologous cell (e.g., a cell from the subject/recipient of an implantable collagen device of the present invention), and/or a xenogeneic cell (e.g., a cell from a source that is a different species than the subject/recipient of an implantable collagen device of the present invention). Exemplary cells include, but are not limited to, embryonic stem cells; determined stem cells; perinatal stem cells; committed progenitors; pluripotent stem cells such as induced pluripotent stem cells; multipotent stem cells such as mesenchymal stem cells and hematopoietic cells; stems cells from adult tissues or cord blood; adult cells of any suitable type such as smooth muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, and adipocytes; tumor cells; and any combination thereof. In some embodiments of the present invention, the stem cells can be obtained without destruction of a human embryo.

One or more cells can be used in the methods and devices of the present invention and when more than one cell is used, the cells can be the same or different. In certain embodiments of the present invention, the at least one cell comprises a mesenchymal stem cell from any source and/or a fibroblast from any source. In some embodiments of the present invention, the at least one cell is a fibroblast from human foreskin and/or a fibroblast from an autograft tissue such as dermis. The term "attach", "attachment", and grammatical variants thereof, as used herein, refer to cellular adhesion and/or binding to a collagen fiber and/or collagen construct. In some embodiments of the present invention, a cell 70 can attach to a collagen construct 60 and/or fiber 60*f* via a cell adhesion molecule 70*a*, such as, but not limited to, selectins, integrins, and/or cadherins, thereby forming an implantable collagen device 60 (FIG. 1).

"Collagen construct," as used herein, refers to a device and/or material that comprises collagen. The collagen construct can be in finished or final form for use or in an unfinished or pre-final form. The collagen construct can comprise natural collagen, natural collagenous tissue, synthetic collagen, and/or any combination thereof. "Synthetic collagen" as used herein, refers to collagen material that has been formed and at least one of chemically or physically created or altered from its naturally-occurring state into an elongate collagen fiber. In some embodiments of the present invention, a collagen construct can be for a tendon or ligament repair. In other embodiments, the collagen construct can be for skin or other tissue repairs or treatments.

Exemplary collagen constructs, include, but are not limited to, collagen fiber patches, such as wound bed patches, muscle or organ patches, cardiac patches, hernia patches, skin patches, burn treatment patches, and skin/tissue repair patches; cuffs; blood vessel (artery, vein, and the like) repair material; valve replacements or valve repair material; autograft material; allo-graft material; xenograft material; nerve guides; tubes; tendon sleeves, such as sleeves that can reside about repairing tendon to prevent or inhibit adhesions; indwelling tubes for delivery of therapeutic agents; ducts, such as lymphatic, hepatic, pancreatic and cystic ducts; tubes, such as ureter and urethra tubes; collagen fiber; collagen gel; sutures; cords; twisted cords; ligament and/or tendon prosthesis; cables; braids; ribbons; staples; rivets; sponges; and the like. Further examples and description of devices are described in U.S. Pat. No. 7,901,455; U.S. Patent Application Publication Nos. 2008/0161917, 2008/0188933, 2008/0200992, 2009/0216233, 2009/0287308, 2010/0094318, and 2010/0094404; U.S. patent application Ser. Nos. 13/153,665 and 13/105,353; and U.S. Provisional Patent Application No. 61/450,179, which are incorporated herein by reference in their entirety.

A collagen fiber or collagen fiber construct can be polymerized with a suitable cross-linking agent. A collagen construct can include elongate fibers that can be polymerized with a suitable cross-linking agent. Exemplary cross-linking agents include, but are not limited to, nor-dihydroguaiaretic acid (NDGA), 3,4-dihydroxyphenylalanine, dopamine, 3,4-dihydroxybenzaldehyde, 3,4-dihydroxybenzoic acid, carbodiimide, glutaraldehyde, formaldehyde, tannic acid, isocyanates, epoxy resins, and cross-linking agents comprising a quinone group and/or a catechol group, such as those described in U.S. Provisional Patent Application No. 61/530,115, on page 13, second paragraph to page 14, first paragraph, this content is incorporated herein.

In certain embodiments of the present invention, the collagen fiber construct, such as, for example, braids, weaves, mandrel-wound fibers, cables, ribbons, staples, patches and rivets, is not polymerized with a cross-linking agent. The collagen fiber construct can comprise a tube that comprises a partially dried collagen gel(s). In other embodiments, the collagen construct comprises a sponge.

In some embodiments of the present invention, the collagen construct comprises at least one synthetic collagen fiber. A synthetic collagen fiber can be an elongate continuous length of fiber formed of denatured (gelatin) and/or non-denatured collagen (e.g., whole or fragmented native collagen fibers from tendon, skin, or other sources). An elongate collagen fiber can have a length of at least about 0.25 inches, typically greater than about 0.5 inches, such as between about 0.5-30 inches, or between about 1-20 inches or between about 1 m to about 100 m.

According to some embodiments of the present invention, a collagen construct comprises at least one elongate collagen fiber which can optionally be polymerized with a suitable cross-linking agent. In some embodiments, the collagen construct comprises a plurality of elongate collagen fibers, which can optionally be polymerized with a suitable cross-linking agent. In certain embodiments, the collagen construct comprises at least one polymerized elongate collagen fiber.

Examples of fiber configurations include a single fiber, a plurality of fibers, a fiber bundle, or a plurality of fiber bundles. The fibers or fiber bundles can be twisted, woven, braided or wound to define a respective twisted, woven, a braided or wound collagen fiber construct. The wound fiber refers to fiber or fibers that can be formed into a construct shape that can define be modified for implantation in a desired shape using a mandrel-wound length of collagen fiber(s). See, e.g., U.S. patent application Ser. Nos. 13/153, 665; 12/576,435; 12/576,423 and PCT/US12/27366 (U.S. Provisional Application Ser. No. 61/450,179), the contents of which are hereby incorporated by reference as if recited in full herein. In some embodiments of the present invention, the collagen construct is a woven "ribbon" construct of warp and weft fibers optionally comprising integrated sutures. Examples of which are shown in FIGS. 2A, 2B, 3A, and 3B.

Figure 2A:
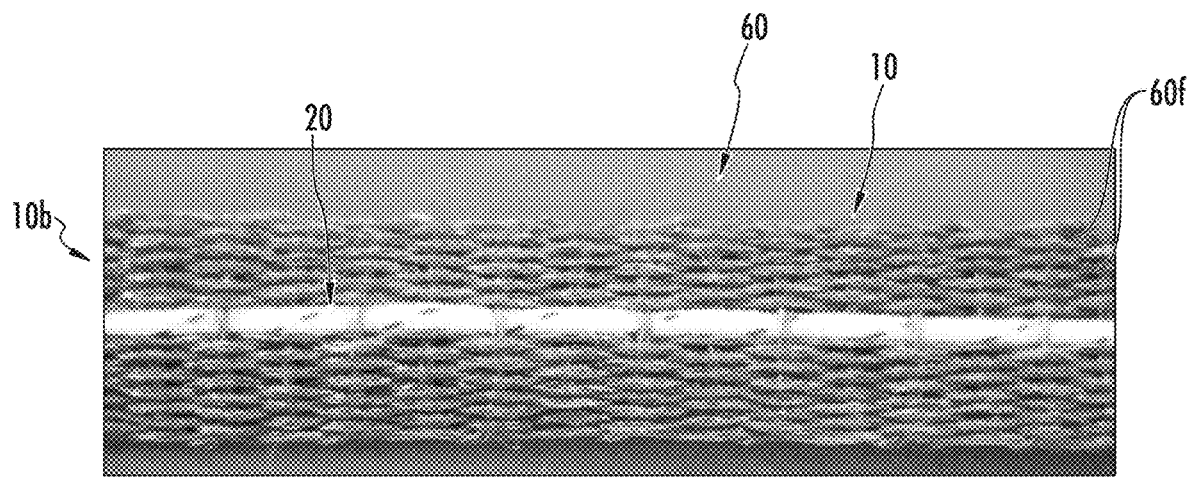
FIG. 2A is a digital photograph of a portion of a collagen construct comprising a ribbon with an integrated suture according to embodiments of the invention.
Figure 2B:
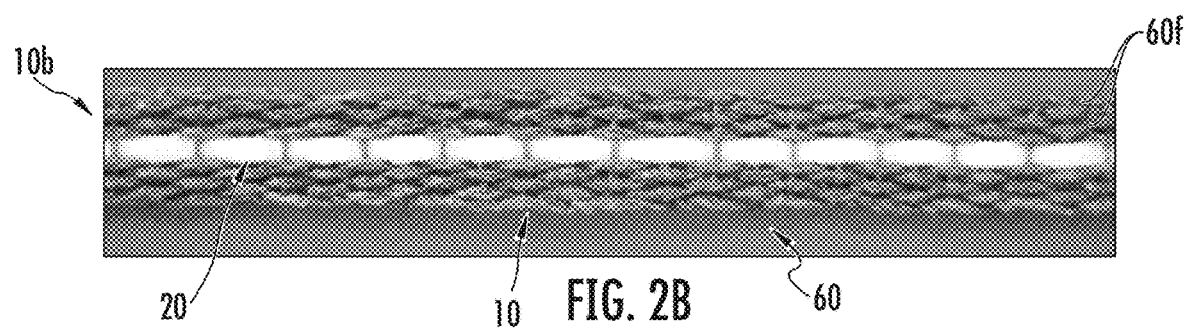
FIG. 2B is a digital photograph of a portion of a collagen construct comprising a narrower ribbon with an integrated suture similar relative to the ribbon shown in FIG. 2A according to embodiments of the invention.

FIGS. 2A and 2B illustrate examples of ribbons 10 as the construct 60 with collagen fibers 60$f$ and at least one integrated suture 20 that extends beyond at least one end of the ribbon body 10$b$, and typically beyond both ends of the ribbon body 10$b$ a distance of at least about 1 inch. The at least one suture 20 can be woven into the weave of the ribbon body 10$b$ without requiring any supplemental fixation members providing for a seamless smooth configuration. FIGS. 2A and 2B illustrate a single (multi-fiber) suture 20 that is woven into an axially extending (lengthwise direction) center portion of the ribbon body 10$b$ and extends substantially straight throughout the length of the ribbon body. Two or more (typically substantially) parallel sutures oriented to extend in the lengthwise direction may also be used instead of the single suture shown. FIGS. 3A and 3B illustrate examples of ribbons 10 with collagen fibers 60$f$ and transversely spaced apart pairs of sutures $20_1$, $20_2$ and $20_3$, $20_4$ woven directly into the ribbon body 10$b$, one pair proximate each opposing outer long side of the ribbon body 10$b$. Further exemplary collagen constructs include those described in U.S. Pat. No. 7,901,455 and U.S. Provisional Patent Application No. 61/450,179, which are incorporated herein by reference in their entirety.

The term "woven" means that the woven construct includes one or more warp and one or more weft yarns, typically between about 10-100 warp and between about 1-10 weft yarns. The woven construct can be a ribbon 10$b$ that can have any suitable number of yarns, any suitable number of fibers 60$f$ in each yarn, and/or any desired number of picks/inch to form the braid pattern. In some embodiments, the ribbons 10 can have a substantially repeating weft pattern with a weft yarn(s) having a cross-over (a frequency) of about every 0.1 mm to about every 25 mm, typically between about every 0.5-10 mm, and more typically in a substantially repeating pattern with a cross over between about every 1-5 mm.

Each yarn in a ribbon 10$b$ can be a single fiber 60$f$ (also known as filament) yarn or multi-fiber (multi-filament) yarn. Some yarns 10$y$ may have more fibers than others in a respective ribbon 10$b$ or all the yarns may have the same number of fibers 60$f$. The fiber 60$f$ or fibers in each yarn(s) may be twisted or untwisted, or combinations of twisted and untwisted may be used for each or respective different yarns within a single ribbon 10$b$.

In some embodiments, the yarns can each have between about 1-100 elongate continuous length collagen fibers (treated to improve strength, such as treated with NDGA), typically between about 2-20 fibers in each yarn. That is, the collagen fibers 60$f$ can have a length sufficient to extend over substantially the entire length of the ribbon body. The ribbons 10$b$ may have between about 1-1000 yarns, typically between about 3-100 yarns some of which are weft and some of which are warp yarns. For example, the ribbon body 10$b$ can include between about 10-100 warp yarns of between about four to eight long NDGA treated collagen fibers 60$f$. The yarn fibers may be twisted or braided together for a respective yarn.

In some embodiments of the present invention, the collagen construct 10 comprises elongate collagen fibers that are wound, woven or braided to form a construct that does not comprise an integrated suture.

FIG. 3C illustrates examples of ribbons as the collagen construct 10. The ribbons 10b may, but are not required to, include an integrated suture. In some embodiments, a woven or braided "ribbon" construct that does not comprise a suture is polymerized with a suitable cross-linking agent, such as, but not limited to, NDGA.

Figure 3D:
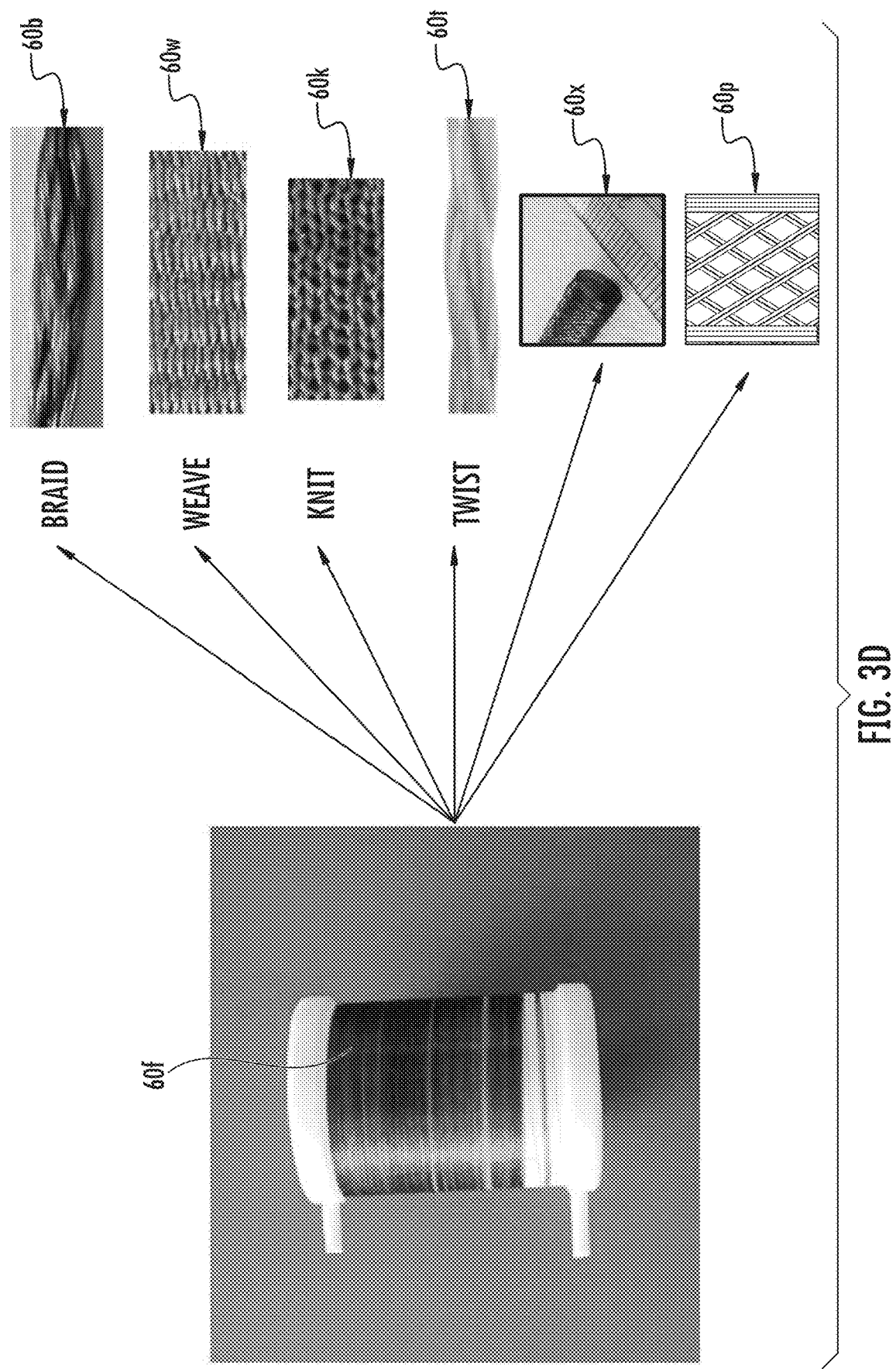
FIG. 3D is a digital photograph of collagen constructs comprising at least one elongate collagen fiber according to embodiments of the invention.

In some embodiments of the present invention, the collagen construct comprises at least one continuous length elongate collagen fiber. FIG. 3D illustrates a collagen construct that comprises an elongate collagen fiber 60f that has been spooled.

FIG. 3D further illustrates that, in some embodiments of the present invention, a collagen construct can comprise a plurality of elongate collagen fibers that can comprise a braided collagen fiber construct 60b, a woven collagen fiber construct 60w, a knitted collagen fiber construct 60k, a twisted collagen fiber construct 60t, a wound collagen fiber construct 60x and a collagen fiber patch 60p.

The term "patch" refers to a piece or segment of biomaterial that can be placed on and/or affixed to target anatomical structure, typically soft tissue, to treat, protect, repair and/or reinforce a target site. The patch can be any geometric shape but is typically substantially planar and may, in position, conform to the shape of underlying or overlying tissue.

The term "implantable" and derivatives thereof, as used herein, means the collagen device can be inserted, embedded, grafted or otherwise acutely or chronically attached or placed in or on a subject.

The present invention finds use in medical applications and medical studies. The term "medical" includes both human and veterinary uses. In some embodiments of the present invention, the collagen device can be implanted in a subject. In other embodiments of the present invention, the collagen device can be utilized in in vitro, ex vivo, and/or in vivo experimental studies.

Suitable subjects for treatment using constructs of the present invention include, but are not limited to, avians and mammals. The term "avian" as used herein includes, but is not limited to, chickens, ducks, geese, quail, turkeys, pheasants, parrots, parakeets, macaws, cocktails, canaries, and finches. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), and mammals in utero. In some embodiments of the present invention the subject is a mammal and in certain embodiments the subject is a human. Human subjects include both males and females of all ages including fetal, neonatal, infant, juvenile, adolescent, adult, and geriatric subjects as well as pregnant subjects.

Generally stated, one or more collagen fibers or a device with a body having one or more collagen fibers is populated (seeded) with cells, such as one or more of embryonic, neonatal or adult cells, pluripotent stem cells, mesenchymal stem cells, tendon and/or ligament fibroblasts, or combinations thereof. The (e.g., stem) cells proliferate to a desired level on the one or more collagen fibers. Then, strain (and/or stress) is applied to the fibers/device or at least one fiber, the cells attached to the fibers and transduce the mechanical strain (deformation) signal which induces them to differentiate into tendon (or ligament, for example) fibroblasts.

Once the cells differentiate, they can proliferate and can also begin to produce an extracellular matrix comprising predominantly collagen. Collagen production is governed by the cyclic strain (and/or stress). The collagen fiber or collagen fibers of the body of the device can include the starting collagen fiber or collagen fiber construct: plus 1) differentiated tendon and/or ligament phenotype cells; 2) differentiated tendon and/or ligament phenotype cells plus a minor amount of extracellular collagen matrix; 3) differentiated tendon and/or ligament cells plus a relatively large amount of extracellular matrix of collagen. The extracellular matrix can be predominantly collagen and may have other molecules and/or proteins, in lesser amounts.

The phenotype of differentiated cells can be evaluated as is known to those of skill in the art based on one or more of cellular, morphologic and/or molecular characteristics and/or expression markers. For example, stem cells are stellated in appearance but when differentiated into fibroblasts with tenocyte morphology, they elongate and align with a direction of collagen fibers and/or fibrils.

Examples of markers for a tendon phenotypic expression include Type I collagen, or Types I and III collagen, expression of scleraxis, and/or a transcription factor associated with the tendon fibroblast phenotype.

The end device or fiber(s) with the collagen fibers, differentiated (phenotype) cells and extracellular matrix can comprise about 95% collagen, dry weight.

Exemplary Methods of Preparing an Implantable Collagen Device

Figure 4:
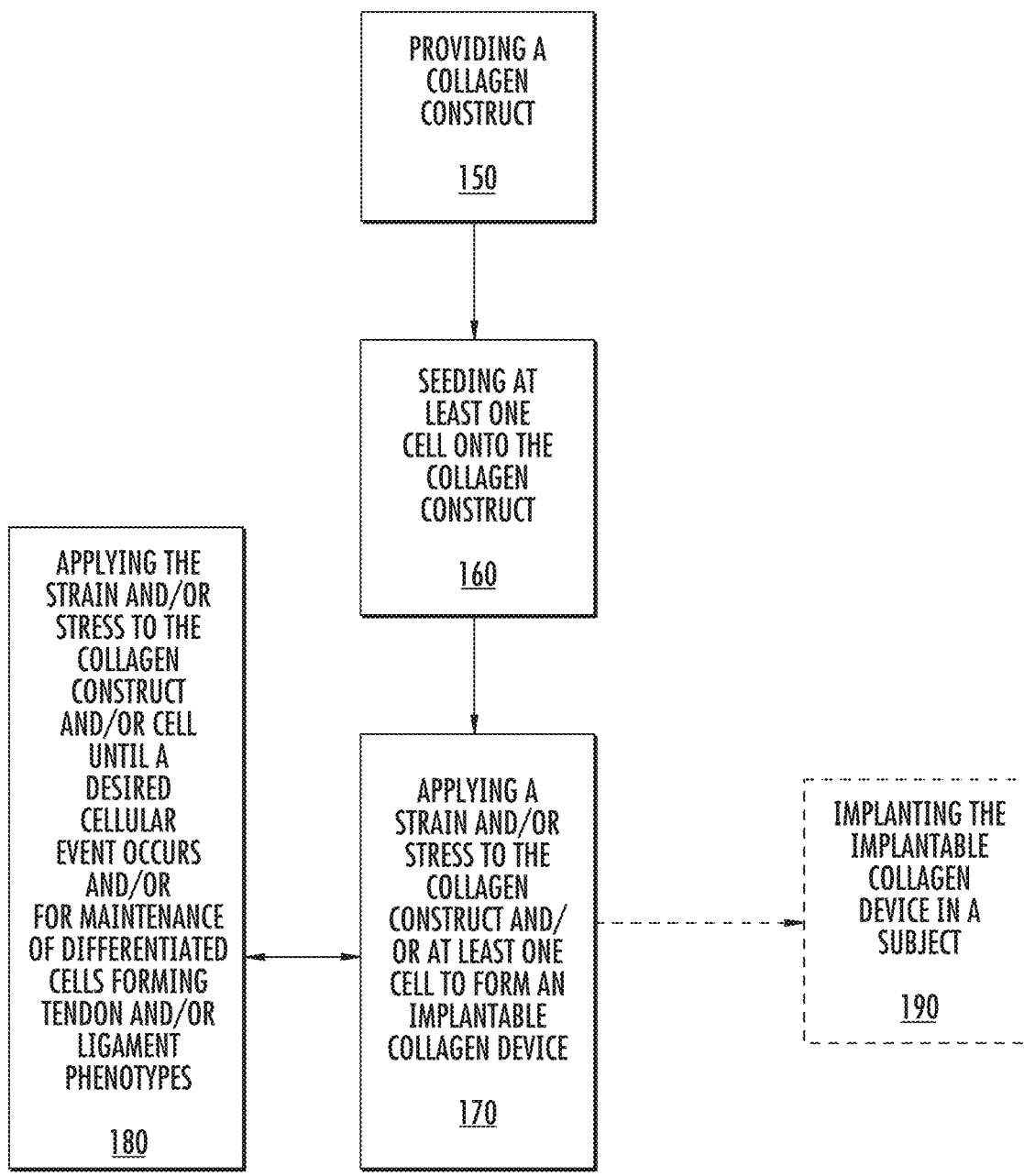
FIG. 4 is a flow chart of operations that can be used to carry out embodiments of the invention.

A further aspect of the present invention comprises methods of preparing an implantable collagen device (FIG. 4) comprising, consisting essentially of, or consisting of providing a collagen fiber construct 60 (block 150), seeding the collagen construct 60 with at least one cell 70 (block 160), and applying a strain and/or stress to the collagen construct 60 and/or at least one cell 70 (block 170), thereby producing an implantable collagen device.

In particular embodiments of the present invention, the strain and/or stress is applied until a desired cellular event(s) occurs. Different strains can be applied. For example a static load or strain can be applied during a seeding and/or post-seeding period until a desired amount of cell proliferation on the at least one collagen fiber has occurred, then a cyclic strain and/or stress can be applied to promote extracellular matrix formation and to maintain cell differentiation (e.g., tendon or ligament phentotype fibroblasts and/or cells).

Figure 5A:
FIG. 5A is a schematic illustration of a side perspective view of a collagen construct comprising an elongate collagen fiber according to embodiments of the invention.
Figure 5B:
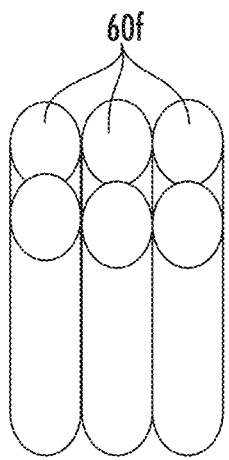
FIG. 5B is a schematic illustration of a side perspective view of a collagen construct comprising a plurality of elongate collagen fibers according to embodiments of the invention.

According to some embodiments of the present invention, the collagen construct 60 can comprise an elongate collagen fiber 60f (FIG. 5A). In other embodiments of the present invention, a plurality of elongate collagen fibers can together form a collagen construct 60 (FIG. 5B). In some embodiments of the present invention, a plurality of elongate collagen fibers are wound, twisted, woven or braided together (FIGS. 2A, 2B, 3A, and 3B). When a collagen construct comprises more than one elongate collagen fiber, each or some of the elongate collagen fibers that form the construct can be seeded with a cell(s) and/or subject to a strain and/or stress.

In some embodiments, the collagen fiber construct is configured to mimic a natural tendon or ligament and can have substantially the same or greater tensile strength and substantially the same elastic modulus. Thus, during cycling, the construct and/or fibers can impart proper strain onto the seeded "starter" cells to promote cellular changes into tendon (or ligament) phenotype cells such that the cells from the cell culture change into tenocyte (or ligocyte)

morphology to have elongated cells aligned with the axial direction of the fibers or fibrils.

Figure 6A:
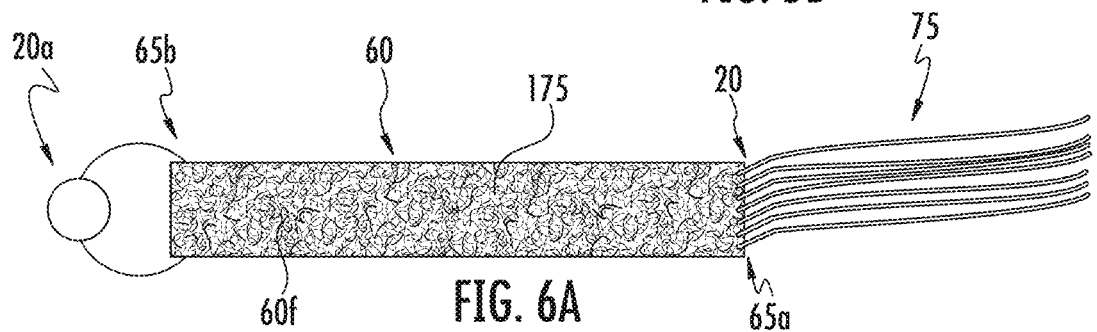
FIGS. 6A-6C are schematic illustrations of implantable collagen devices in position in a subject according to embodiments of the invention.
Figure 6B:
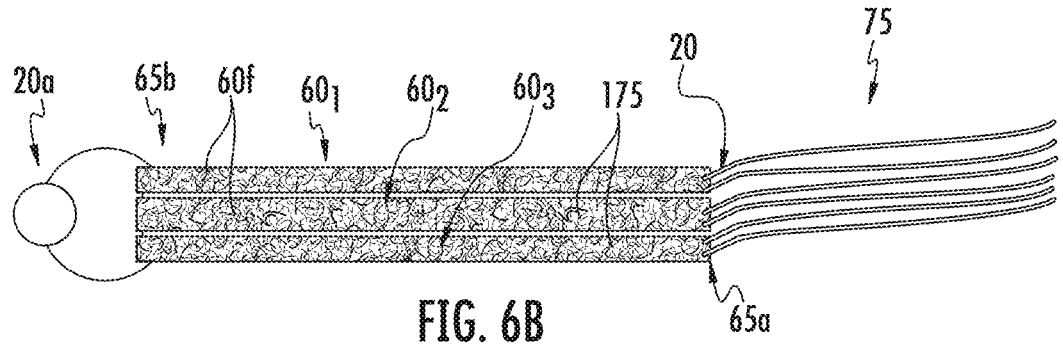
Figure 6C:
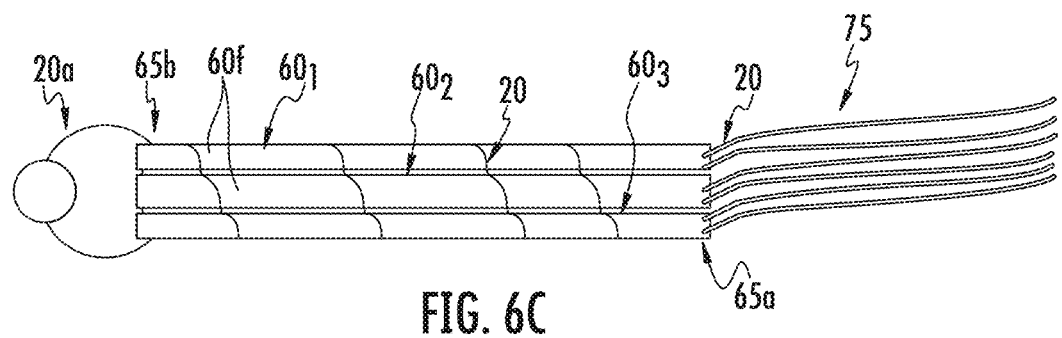

An implantable collagen device can be used (e.g., implanted) on its own or in combination with one or more implantable collagen device(s). As shown in FIG. 6A, an implantable collagen device 60 having at least one collagen fiber 60f of any size or shape, can be implanted in a subject as a tendon repair with a first end portion 65a attached to a tissue 75 via a suture 20 and a second end portion 65b attached using a suture anchor 20a. In other embodiments of the present invention, one or more implantable collagen devices of any size or shape can be implanted next to and/or on top of one another. As shown in FIG. 6B, a plurality of implantable collagen devices $60_1$, $60_2$, and $60_3$, of any size or shape, are implanted in a subject as a tendon repair with a first end portion 65a attached to a tissue 75 via a suture 20 and a second end portion 65b attached using a suture anchor 20a. The one or more implantable collagen devices 60 can be sewn together, such as with an integrated suture 20 (FIG. 6C). The embodiments shown in FIGS. 6A-6C are for example only. Both ends of the construct 60 can be implanted, attached or anchored in the same manner, e.g., using a suture, or in different manners as is known to those of skill in the art.

In preparing an implantable collagen device of the present invention, at least one cell is seeded onto a collagen construct. The term "seed", "seeding", and grammatical variants thereof as used herein, refer to one or more defined cells being contacted, placed on, and/or loaded onto a collagen construct. Before, during, and/or after the seeding step, the collagen construct can be maintained under cell culture conditions. During and/or after the seeding step and/or culturing, the at least one cell can attach to the collagen construct. In particular embodiments of the present invention, a collagen construct is seeded with at least one cell, such as, for example, at least one mesenchymal stem cell from any source and/or a fibroblast from any source.

At least one (e.g., a clonal cell), typically at least a few cells to 100s of cells, or 1000s or more cells can be driven to reproduce to proliferate, populate and attach to fiber attachment sites so that substantially all or at least a majority of available attachment sites are filled with the "starter" cells. Non-attached cells can be washed away or otherwise removed. The cells can attach to cover substantially an entire, or at least a majority of, the surface area of each elongate fiber.

Cell culture media suitable for the methods of the present invention are known in the art and include, but not limited to, Dulbecco's Modified Eagle's Medium (DMEM), Dulbecco's Modified Eagle's Medium high glucose (DMEM-H), McCoy's 5A Modified Medium, and Medium 199. The cell culture medium can be supplemented with additional components such as, but not limited to, vitamins, minerals, salts, growth factors, carbohydrates, proteins, serums, amino acids, attachment factors, cytokines, hormones, antibiotics, therapeutic agents, buffers, etc. The cell culture components and/or conditions can be selected and/or changed during the methods of the present invention to enhance and/or stimulate certain cellular characteristics and/or properties. Examples of seeding methods and cell culturing methods are described in U.S. Pat. Nos. 5,266,480, 5,770,417, 6,537,567, and 6,962,814 and Oberpenning, F., et al., De novo reconstitution of a functional mammalian urinary bladder by tissue engineering, Nature Biotechnology, 17, 149-155 (1999), which are incorporated herein by reference in their entirety.

The cell seeding and/or culturing can be carried out in a sterile environment using equipment and methods known in the art. In some embodiments of the present invention, the temperature of the cell seeding and/or culturing environment is between about 25° C. to about 40° C. or any range therein, such as between about 30° C. to about 40° C. or between about 35° C. to about 40° C. In particular embodiments of the present invention, the temperature of the cell seeding and/or culturing environment is about 37° C. The cell seeding and/or culturing environment can be at atmospheric pressure, reduced pressure (e.g., vacuumized pressure), high pressure, and/or any combination thereof. In particular embodiments of the present invention, the pressure of the cell seeding and/or culturing environment is atmospheric pressure. In some embodiments of the present invention, the cell culturing and/or seeding steps are carried out in an atmosphere of between about 2% to about 20% carbon dioxide ($CO_2$) or any range therein, such as between about 5% to about 10% or between about 5% and about 15% $CO_2$. In particular embodiments of the present invention, the cell seeding and/or culturing are carried out in an atmosphere of between about 5% to about 10% $CO_2$. Other gases, such as, but not limited to, nitrogen and/or oxygen, can be added to the cell seeding and/or culturing atmosphere. In some embodiments of the present invention, one or more gases can be used to obtain and/or maintain the desired atmosphere (e.g., to maintain the desired oxygen and/or carbon dioxide levels).

In some embodiments of the present invention, the seeding step is carried out two or more times, such as between 2-20 times, including 2, 3, 4, 5, 6, 7, 8, 9 or more times, during the preparation of an implantable collagen device of the present invention. For example, a collagen construct can be seeded with at least one cell and the cell can be cultured for a period of time. Then, the collagen construct can be seeded a second time with at least one cell that is the same as or different than the first cell(s). In some embodiments of the present invention, a cell culturing step is not necessary after the seeding step when a desired cell confluency is obtained on a collagen construct after the seeding step.

According to some embodiments of the present invention, during and/or after seeding and/or cell culturing, a collagen construct and/or cell(s) can be subjected to a force loading. "Force loading" as used herein refers to a tensile, strain and/or stress load on a collagen construct and/or cell(s). The strain and/or stress can be a direct and/or indirect force that is created by mechanical, fluid, and/or electrical means. In some embodiments of the present invention, a collagen construct and/or cell is subjected to a stress or a strain. In embodiments of the present invention, a collagen construct and/or cell is subjected to a stress and a strain in any order and/or combination. Those skilled in the art will appreciate that a stress on a collagen construct and/or cell can cause a strain on the collagen construct and/or cell.

While embodiments of the invention contemplate the use of flexible packages, e.g., elastomeric and/or polymeric pouches to hold the at least one collagen fiber or collagen fiber construct during the seeding and applying of strain/stress to induce the cellular events, conventional cell culture vessels may also be used for such purpose.

In some embodiments, as shown in FIG. 13E, the mounted construct (typically in the package/bag/pouch as shown in FIG. 14A/B) is pulled from each end to remove slack. An inter-clamp distance $D_1$ is defined or measured, and an initial relatively low offset strain Ti of a desired amount, e.g., about 1% can be applied. Cyclic strain can then be applied as shown in the timing diagram associated with FIG. 14B. The magnitude of strain can vary between 2% and 10%. The construct can substantially always be held under tension, going from the initial offset to a desired strain. So the cyclic tension goes from 1% to say 11% at a defined frequency (such as those stated herein). The associated distances between clamps $D_2$ and $D_3$ can be used to control the tension/strain during cycling. One distance can apply the maxima cyclic strain $Tc_1$ or tension and the other $D_3$ can apply a lower cyclic strain or tension $Tc_2$ that is still above the initial offset strain or tension Ti associated with distance $D_1$.

In some embodiments, the loading can be carried out to apply stress. The construct is loaded to reach a defined percent of a known failure load, typically about 1% of its failure load (the actual load will differ depending on the size of the construct). Then additional load is applied cyclically to increase and decrease loading at a defined frequency. The applied load can vary from 2% of failure load to about 50% of failure load. The frequency can be constant over a defined time or may vary, e.g., from 10 Hz to 5 Hz over different time periods during the cellular events or for maintenance of the cell differentiation.

It is contemplated that the loading can be carried out to induce one or more of three outcomes. The cyclic tension and/or strain can continue until at least one of the following outcomes occurs: (i) the construct is populated by cells that have been 'differentiated' into tendon or ligament phenotype cells, typically with an extracellular matrix of collagen; (ii) a thickness of the construct or height of organized cells/tissue is sufficient so as to increase a thickness of the construct by between 10-200%, e.g., the cells can increase the thickness of the collagen fiber construct itself as cells populate, differentiate into tendon or ligament phenotypes and/or organize and produce a tendon-like tissue; or (iii) the construct has a large extracellular matrix of collagen or predominantly collagen (more collagen than other molecules and/or proteins), e.g., an amount greater than the ligament or tendon phenotype cells.

In some embodiments, tissue may be expected to grow over the entire construct between the points where it is clamped (if clamping is used to hold the device/provide the loading). It is contemplated that the phenotype cells and extracellular matrix of tissue can at least double the thickness of the construct. For example, a thickness or height of organized cells/tissue on the collagen fibers is sufficient so as to increase a thickness of the construct by between 10-200%, e.g., the phenotype cells and/or extracellular matrix can double or increase the thickness fiber construct itself as cells grow and organize and produce a tendon-like tissue.

A tensile load, strain and/or stress can be uniaxial, biaxial, multiaxial, or any combination thereof. In particular embodiments, the strain and/or stress is uniaxial. In some embodiments of the present invention, during the method of preparing an implantable collagen device of the present invention, the strain and/or stress can be in the same direction throughout the fabrication. Alternatively, the strain and/or stress can change directions during the fabrication. For example, in some embodiments of the present invention, the strain and/or stress is uniaxial along the horizontal axis of a collagen construct throughout the method of preparing a collagen fiber and/or implantable collagen fiber device.

In some embodiments of the present invention, the strain and/or stress is uniaxial along a long or short axis, e.g., a long or short horizontal axis of a collagen construct for a period of time, then changes to uniaxial along the short or long vertical axis of the collagen construct for a period of time.

The strain and/or stress can directly and/or indirectly contact a cell and/or can be directly and/or indirectly transmitted to a cell. The strain and/or stress can cause strain and/or stress within a cell body and/or can result in and/or initiate cell signaling within a cell and/or between one or more cells and/or their environment. The strain and/or stress can cause changes to occur within a cell and/or the cellular membrane (e.g., changes in the cytoskeleton and/or cytoplasm, clustering of membrane receptors, etc.). The strain and/or stress can change, alter, and/or regulate cell to cell interactions, cellular interactions with the extracellular matrix, and/or the extracellular matrix. In some embodiments of the present invention, the strain and/or stress can cause a cell to change its phenotype (e.g., differentiate) and/or the extracellular matrix. In particular embodiments of the present invention, a strain and/or stress causes a cell to differentiate into a particular type of cell (e.g., a fibroblast, etc.). In certain embodiments of the present invention, a strain and/or stress causes a cell to form a tissue (e.g., a connective tissue, a muscle tissue, etc.).

Exemplary types of actions that can be used to provide the strain and/or stress include, but are not limited to, tension, pressure, compression, shearing, torque, elastic deformation, brittle deformation, ductile deformation, or any combination thereof. In some embodiments of the present invention, during the method of preparing an implantable collagen device of the present invention, the strain and/or stress can be the same type throughout the method or can change during the method. In certain embodiments of the present invention, the strain and/or stress is applied in the form of a tensile strain and/or stress in and/or across a collagen construct and/or cell. In other embodiments of the present invention, the strain and/or stress is applied in the form of a pressure, such as, but not limited to, a hydrostatic pressure, and/or a compressive force on a collagen construct and/or cell. In certain embodiments of the present invention, the strain and/or stress is applied in the form of a shear strain and/or stress, pressurized fluid, and/or flow vectors. In particular embodiments, the shear strain and/or stress can be created by altering a flow of a fluid across the surface of a collagen construct and/or cell.

The strain and/or stress can be static and/or cyclic. The term "static", as used herein, refers to a strain and/or stress that is constant or substantially constant for a period of time. The term "substantially constant", as used herein, refers to a strain and/or stress that on average changes by less than 1% over a defined period of time, such as about 1 minute, 5 minutes, 10 minutes, 1 hour, 24 hours, and the like. Those skilled in the art will appreciate that a static strain and/or stress can created by gradually or quickly increasing the strain and/or stress applied to a collagen construct and/or cell until the desired level of strain and/or stress is achieved, then a constant or substantially constant strain and/or stress can be maintained for a period of time and after this period of time the static strain and/or stress can be gradually or quickly removed resulting in a decreasing strain and/or stress.

In particular embodiments of the present invention, the strain and/or stress is cyclic for at least part of a fabrication period, particularly during and/or after seeding. The term "cyclic", as used herein, refers to a strain and/or stress that varies (increases and decreases) in magnitude by a defined amount over a defined period of time. A cyclic strain and/or stress can cycle between about 0.1 Hz to about 10 Hz over a period of time (e.g., hours or days) or any range therebetween, such as between about 0.5 Hz to about 8 Hz or between about 1 Hz to about 5 Hz. In some embodiments of the present invention, the cyclic strain and/or stress cycles at about 0.1, 0.2, 0.3, 0.4, 0.5, 0.6, 0.7, 0.8, 0.9, 1, 2, 3, 4, 5, 6, 7, 8, 9, or 10 over a period of time, e.g., per second, minute, per hour or per day. In particular embodiments of the present invention, the cyclic strain and/or stress cycles at between about 1 Hz or at about 4 Hz.

In some embodiments, an initial strain can be applied, e.g., a low initial offset strain of between about 0.5% to about 1%. Then, cyclic strain can be applied for a defined time. The variation in magnitude of a cyclic strain can be between a value above the initial offset strain, such as between 1%-2% to about 25% (e.g., the strain on the collagen construct and/or cell) or any range therein. In some embodiments, the magnitude of strain can vary between 2% to 12%, between about 5% to about 20%, or between 2% to about 10% of the strain and/or stress. In some embodiments of the present invention, the maximum variation in magnitude of the strain is about 4, 5, 6, 7, 8, 9, 10, 11, 12, 13, 14, 15, 16, 17, 18, 19, 20, 21, 22, 23, 24, or 25%. In particular embodiments of the present invention, the change in magnitude of the cyclic strain can vary between 2% to 10%.

Stated differently, a cyclic tension can be applied so that the construct is always under tension in a defined time frame and cycles between increased tension and a lower tension at a defined frequency over a defined time period. In some embodiments, the tension can increase to cycle between tensile loads that is between 1% above to about 15% above an initial or "base" tensile load Ti (sufficient to remove slack), typically during a cell growth or maintenance period(s). In some particular embodiments, a cyclic tension load is applied so that tension increases by between about 2% to 11% from the base or defined initial load at a defined frequency (which can be the same or change over time) for a defined time period.

In some embodiments, stress can be applied. The construct can be loaded (held in tension) at a defined % of its failure load (the actual load can vary depending on construct size and configuration). Additional load can be applied cyclically. The additional applied load can vary from between 2% to about 50% of the failure load.

The static and/or cyclic strain and/or stress can be applied over a desired period of time. For example, a static and/or cyclic strain and/or stress can be applied over minute(s), hour(s), day(s), week(s), and/or month(s). In some embodiments of the present invention, a static and/or cyclic strain and/or stress is applied throughout the method of preparing an implantable collagen device of the present invention. In other embodiments of the present invention, a static and/or cyclic strain and/or stress is applied intermittently and/or at regular time periods during the method of preparing an implantable collagen device of the present invention.

In some embodiments of the present invention, a collagen construct and/or cell are subjected to strain and/or stress prior to seeding the cell on the collagen construct. In particular embodiments of the present invention, a collagen construct can be formed under strain and/or stress. After formation of the collagen construct, the strain and/or stress on the collagen construct can be maintained, changed, or removed until seeding.

In some embodiments, after seeding, and typically after cell attachment to the collagen fiber or fibers, a collagen fiber, construct and/or cell thereon can be subjected to a strain and/or stress. The strain and/or stress during seeding can be the same or a different type and/or amount of strain and/or stress as the strain and/or stress applied during the formation of the collagen construct. In particular embodiments of the present invention, seeding is carried out with the same type and/or the same amount of strain and/or stress utilized during the formation of the collagen construct. For example, in some embodiments of the present invention, the collagen construct is a collagen fiber braid or weave in which the collagen fibers are formed (woven or braided) under a defined (e.g., static) tensile load. Once the collagen fiber woven or braided construct is formed, the same load can be used during formation (e.g., braiding/weaving) can be applied to the collagen fiber construct. In some embodiments, the same load is applied after seeding. In some embodiments, the same load is applied before seeding. In some embodiments, the same load is applied during seeding and for a time after seeding.

Figure 7:
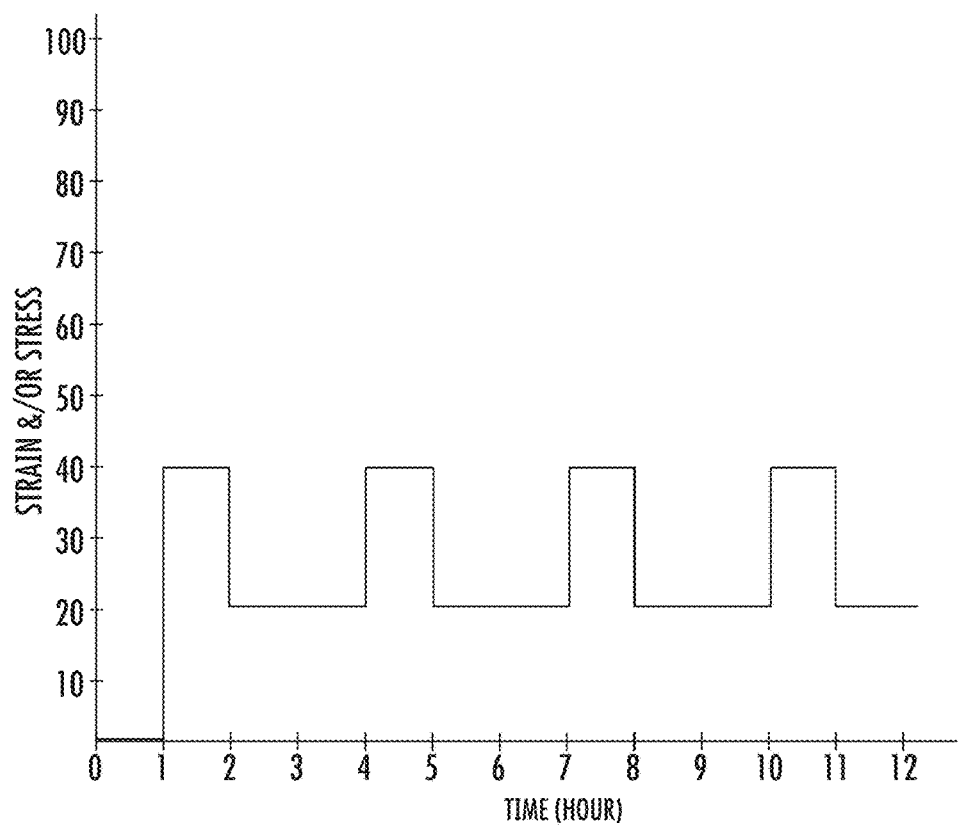
FIG. 7 is a graph of time (hour) v. strain and/or stress showing no application of strain and/or stress during seeding. The strain and/or stress is a prophetic example and the units of the strain and/or stress are nonspecific and used only to show the change in the strain and/or stress over time (hour).
Figure 8:
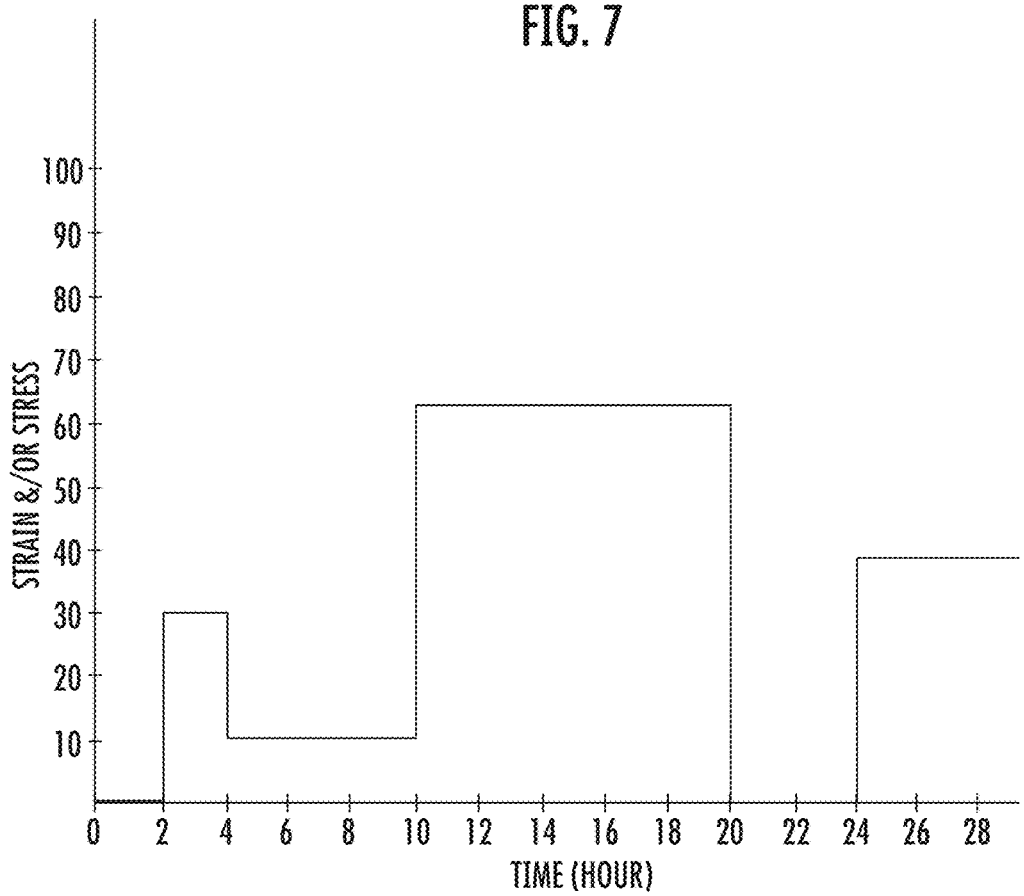
FIG. 8 is a graph of time (hour) v. strain and/or stress showing varying amounts of strain and/or stress for varying amounts of time after seeding. The strain and/or stress is a prophetic example and the units of the strain and/or stress are nonspecific and used only to show the change in the strain and/or stress over time (hour).

In some embodiments of the present invention, a collagen construct (e.g., a construct of one or more collagen fibers or just one or more collagen fibers) is not under strain and/or stress during seeding (but is typically held in tension). After seeding, in some embodiments, no strain and/or stress is applied to a collagen construct and cell proximate thereto for a defined time. This time can be between about 1 hour to about 1 week. In particular embodiments of the present invention, after seeding, no strain and/or stress is applied to a collagen construct and cell until one or more cells attach to the collagen construct and/or until a desired confluency is obtained on the collagen construct. For example, as shown in FIG. 7 no strain and/or stress is applied to a collagen construct during seeding (t=0) and no strain and/or stress is applied until a defined post-seed time, t=1, e.g., shown for example only, is about 1 hour after seeding. Subsequently at t=2, e.g., a static strain and/or stress can be applied for defined time, e.g., about 1 hour. The amount of the static strain and/or stress can be decreased to a lower static strain and/or stress for about 2 hours. This pattern of strain and/or stress can be repeated for a desired amount of time. The lower strain and/or stress can be applied for a greater than, less than, or equal amount of time compared to the period of higher strain and/or stress. Thus, a collagen construct and/or cell proximate thereto can be exposed to varying amounts of strain and/or stress for varying amounts of time (FIG. 8).

Figure 9:
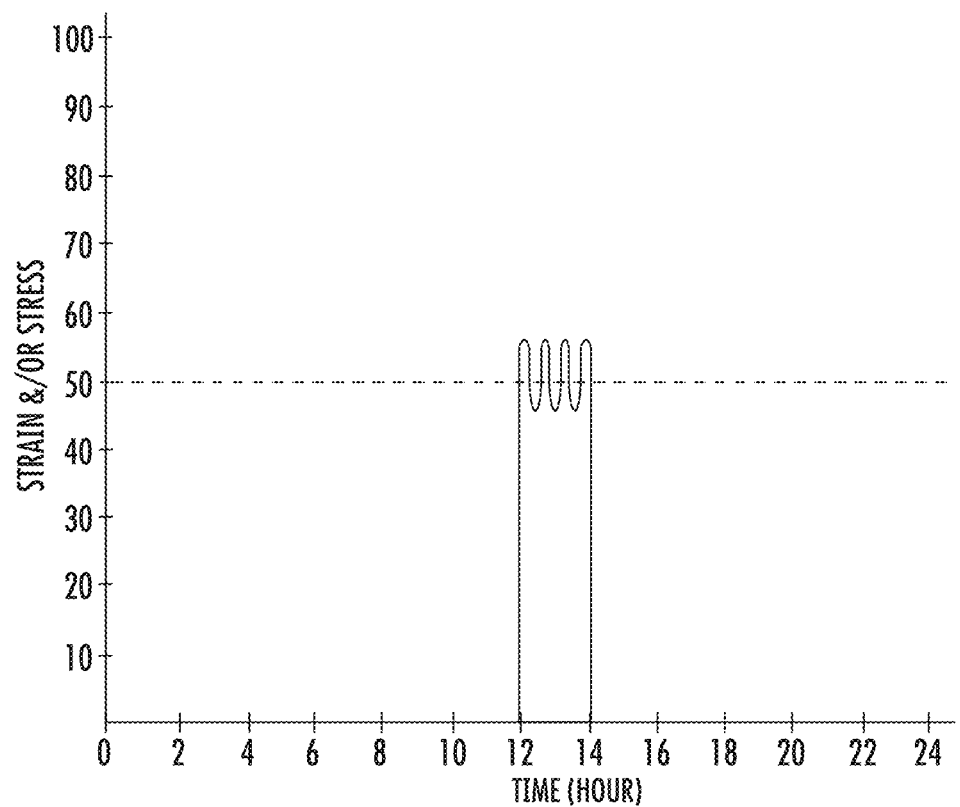
FIG. 9 is a graph of time (hour) v. strain and/or stress showing no application of strain and/or stress until 12 hours after seeding. The strain and/or stress is a prophetic example and the units of the strain and/or stress are nonspecific and used only to show the change in the strain and/or stress over time (hour).

In some embodiments, no strain and/or stress is applied to a collagen construct during seeding (t=0). Then, after an initial (static or cyclic) strain and/or stress is applied, either a lower static or cyclic strain and/or stress is applied or no strain and/or stress is applied to the collagen construct and/or cell. As can be seen FIG. 9, no strain and/or stress is applied to a collagen construct during seeding (t=0) and no strain and/or stress is applied until about 12 hours after seeding (t=12). At about t=12 hours, a cyclic tensile load or strain and/or stress is applied for about 2 hours. Then at about t=14 hours no strain and/or stress is applied. This pattern of strain and/or stress can change and can be repeated for a desired amount of time.

Figure 10:
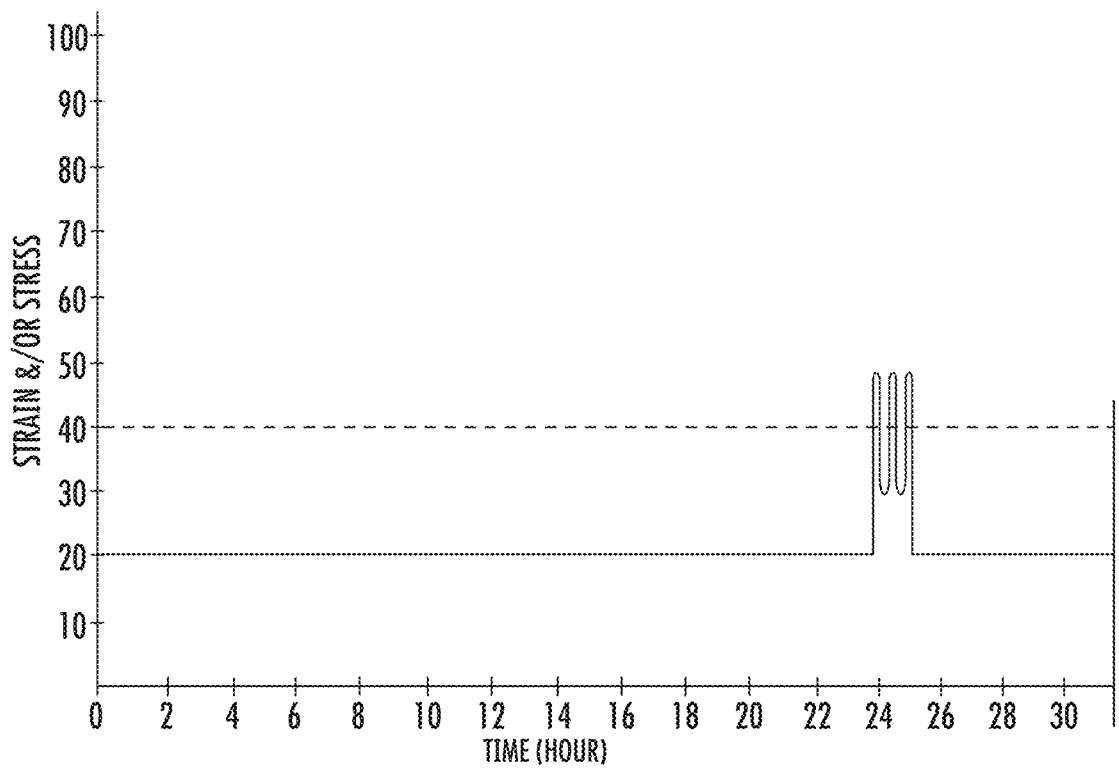
FIG. 10 is a graph of time (hour) v. strain and/or stress showing application of a static strain and/or stress during seeding. The strain and/or stress is a prophetic example and the units of the strain and/or stress are nonspecific and used only to show the change in the strain and/or stress over time (hour).

In certain embodiments of the present invention, a collagen construct is under a static or cyclic strain and/or stress during seeding (t=0). After seeding, a static or cyclic strain and/or stress or no strain and/or stress can be applied to the collagen construct and cell(s). As can be seen in FIG. 10, a static strain and/or stress is applied during seeding (t=0) and this load can remain constant for a defined time, e.g., about 24 hours (t=24). As shown, at about t=24 hours, a cyclic strain and/or stress is applied for about 1 hour. As shown, at about t=25 hours (t=25), a low static strain and/or stress can be applied. This or other pattern of strain and/or stress can be repeated for a desired amount of time.

In some embodiments of the present invention, a (static and/or cyclic) strain or stress is applied to a collagen construct and/or cell proximate thereto for between about 5 minutes to about 24 hours per day for between about two days to about 2 months. Typically, the application of a static and/or cyclic strain and/or stress will continue until a short period prior to use, e.g., providing a shelf life of about 6 hours to about 1 week, once stopped. In certain embodiments of the present invention, at least one cell (typically many cells) is seeded onto a collagen construct under a static strain and/or stress, then after a period of time sufficient for cell attachment and proliferation to a desired level, such as between about 5 minutes to about 48 hours, a cyclic strain and/or stress is applied to the collagen fibers or collagen construct and/or cell(s).

In particular embodiments of the present invention, a cyclic strain and/or stress is applied to a collagen construct and/or cell(s) for between about 5 minutes to about 4 hours per day for about two days to about 2 months. In some embodiments of the present invention, a cyclic strain and/or stress is applied to a collagen construct and/or cell(s) for about 10 to about 30 minutes per day, wherein the cyclic strain and/or stress varies in magnitude by between about 5% to about 15% and at between about 1 Hz to about 2 Hz, and for the remainder of the day, no strain and/or stress is applied to the collagen construct and/or cell(s) or a static load, e.g., static strain is applied to the collagen construct and/or cell(s).

In some embodiments of the present invention, a static and/or cyclic strain and/or stress is applied to a collagen construct and/or cell(s) until a desired cellular event occurs (e.g., cell differentiation, change in the cellular morphology and/or the extracellular matrix, production of an extracellular matrix and/or a tissue that resembles normal tissue, such as a tendon, etc.). In certain embodiments of the present invention, a static and/or cyclic strain and/or stress is applied to a collagen construct and/or cell(s) until a tissue is formed on the collagen construct. In particular embodiments of the present invention, the tissue formed on the collagen construct resembles a tendon or a ligament tissue.

The term "tissue", as used herein in reference to a tissue formed on a collagen construct, refers to a two or three dimensional mass of living tissue that can be produced by in vitro and/or ex vivo cellular growth according to the methods of the present invention. A tissue formed on a collagen construct according to the methods of the present invention can also be referred to as a tissue engineered construct. The tissue can form around and/or through a collagen construct. A tissue engineered construct can comprise the same type of cells or different types of cells. A tissue engineered construct can comprise one or more types of tissue (e.g., connective tissue, muscle tissue, epithelial tissue, etc.). Exemplary tissue engineered constructs include, but are not limited to, a tendon, a ligament, a muscle, an organ, or any combination thereof. In particular embodiments of the present invention, a tendon or a ligament is formed according to the methods of the present invention. In some embodiments of the present invention, a static and/or cyclic strain and/or stress causes one or more cells to produce and/or differentiate to form a tendon or a ligament.

In certain embodiments of the present invention, the implantable collagen device has a tensile strength, stiffness, and/or dynamic flexibility that meets or exceeds that of a natural tissue the device is designed to mimic, such as a tendon or ligament.

After formation of an implantable collagen device according to the methods of the present invention, the implantable collagen device can be implanted in a subject within a defined shelf life of the device, typically within about two months. In certain embodiments of the present invention, the implantable collagen device can be implanted in a subject about 2 to 3 weeks after formation. In some embodiments of the present invention, a static and/or cyclic strain and/or stress can be applied to a implantable collagen device after formation until a short time before implantation (e.g., less than about 1 week) to maintain the differentiated cell status of the attached phenotype cells on the implantable collagen device and/or collagen fiber(s).

The methods of the present invention can be carried out in a package designed to accommodate one or more steps of the methods of the present invention (e.g., seeding, culturing, strain and/or stress, and storage) and the package can comprise one or more collagen constructs, such as 2, 3, 4, 5, or more. The package can be sealable via a seam, flap, adhesive, lid, cap, and/or the like. The package can be a flexible package that can be configured to allow seeding and/or cell culturing and/or cooperate with a device to apply a strain and/or stress to a collagen construct and/or cell. Exemplary means for carrying out seeding and/or cell culturing include but are not limited to, a fluid port, a gas port, a gas exchange port, a pressure valve, and the like. The package can attach to a device to apply the strain and/or stress using, for example, but are not limited to, one or more of clamps, hooks, clips, staples, sutures, an electrical lead, a fluid port(s), a gas port(s), a pressure or vacuum chamber that holds the package (e.g., flexible pouch) and/or the like.

In certain embodiments of the present invention, a means for applying strain and/or stress comprises a mechanical device that can apply tension and/or compression. One or more end portions (typically two opposing end portions) of a collagen construct held in a package is attached to a mechanical device such as a tension mechanism ("tensioner"), in order to apply tension, strain and/or stress to the collagen construct.

In particular embodiments of the present invention, a package allows for a collagen construct to be placed in the package such that the collagen construct does not touch the sides of the package. In other embodiments of the present invention, the collagen construct is freely mobile in the package and can optionally be fixed during application of a strain and/or stress. In some embodiments, opposing ends of the construct and/or fiber(s) are clamped against outerwalls of the package and the package and fibers/construct can move in concert during application of strain/stress. In some embodiments, the fiber(s) and/or construct are encased inside the package. In other embodiments, outer opposing ends of the at least one fiber or fiber construct can reside outside the package and connect to an automated tensioner.

Figure 11A:
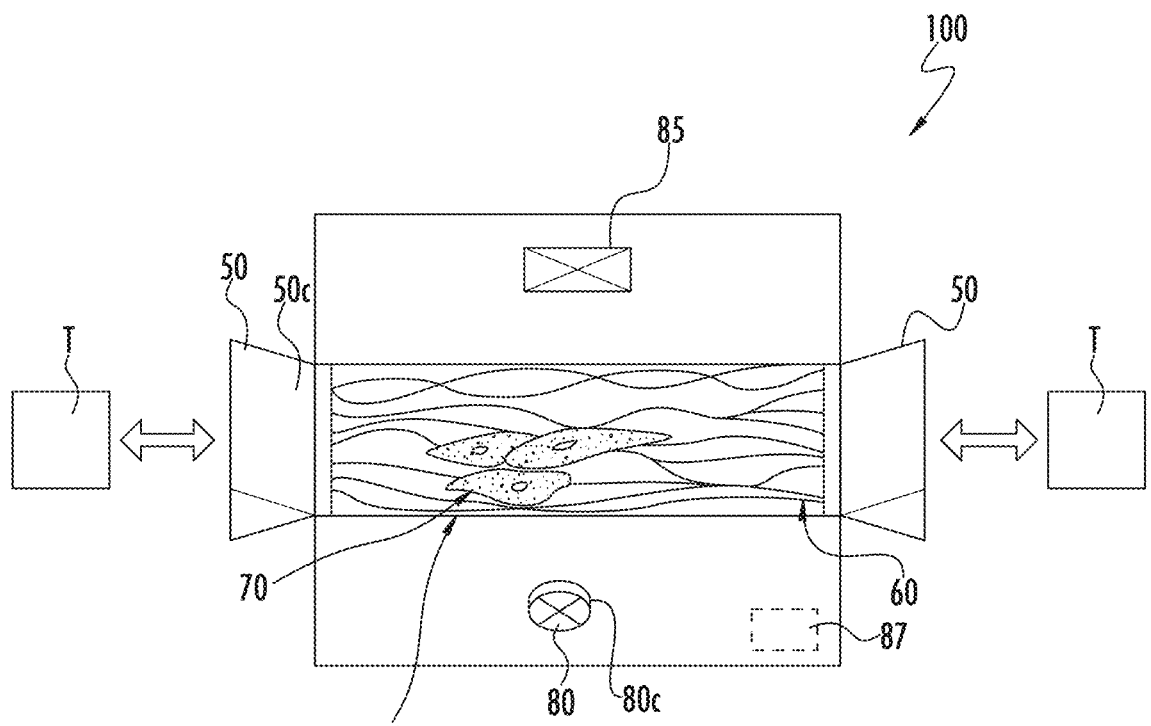
FIG. 11A is a schematic illustration of a device that can provide tension to a collagen construct while seeding and/or culturing according to embodiments of the invention.

As shown in FIG. 11A, a collagen construct 60 can be placed in a vessel, e.g., a package 100 before, during, and/or after seeding. In certain embodiments of the present invention, a package 100 can cooperate with a holding member 50 such as a clamp 50c that can attach to a collagen construct 60 contained within the package 100. The holding member 50 can attach to a tensioner device T that provides tension, strain and/or stress to a collagen construct 60 and/or cell 70. The package 100 can be a flexible pouch of one or multiple layers of material(s). The package 100 can be translucent or transparent or comprise a transparent or translucent window to allow an optical or visual access to internal content to assess seeding and/or cell or tissue formation.

The package 100 can comprise at least one fluid port 80 to allow for the addition and/or removal of cells and solutions, such as cell culture media. The fluid port 80 can be capped 80c or otherwise sealed when not in use. At least one gas exchange port 85 can be included in the package. The gas exchange port 85 can be separate from the fluid port cap

Figure 11B:
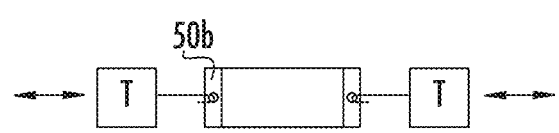
FIGS. 11B and 11C are schematic illustrations of alternate embodiments of a device that can provide tension to a collagen construct while seeding and/or culturing according to embodiments of the invention.
Figure 11C:
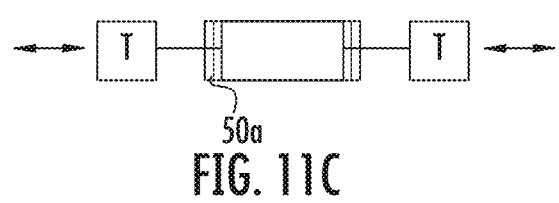

80c or be defined in part of the fluid port cap 80c. A package can comprise an indicator and/or label 87 showing the shelf life of the implantable collagen device 60 in the package and/or the date and/or time the implantable collagen device 60 in the package was prepared. FIG. 11B illustrates that the holding member 50 can comprise a hook and aperture 50h, while FIG. 11C illustrates that the holding member 50 can comprise an adhesive collar or band 50a. The holding member 50 can have other configurations including attachment can be via frictional engagement, adhesive engagement, crimping, clamping, hooking, or other suitable attachment means.

In some embodiments of the present invention, the package can be sterile and/or can provide a sterile environment for cell seeding, culturing, and/or construct storage or shipment. The interior surfaces of a package can be treated to prevent and/or inhibit cell adhesion to the interior surfaces of the package.

A package can comprise materials suitable for cell culture and/or for the application of strain and/or stress. In some embodiments of the present invention, the package is a pouch of an elastomeric, polymeric or other suitable flexible material such that it is substantially impermeable and is capable of being stretched. In particular embodiments of the present invention, a package is a single use, disposable package. In other embodiments of the present invention, a package is capable of being reused and in some embodiments is capable of being sterilized by methods known in the art.

According to some embodiments of the present invention, a method of making an implantable collagen device comprises: placing a collagen construct in a package (e.g., a pouch, bag, container, vessel, etc.); optionally holding the collagen construct in a defined orientation in the package; seeding the collagen construct with a plurality of cells; and applying a strain and/or stress to the at collagen construct to induce the cells to organize into a tissue, thereby producing an implantable collagen fiber construct. In particular embodiments of the present invention, the sealable package comprises at least one fluid port and can optionally be flexible. In some embodiments of the present invention, the collagen construct comprises at least one elongate collagen fiber. Seeding of the collagen construct in the package can be carried out via methods known in the art. In some embodiments of the present invention, seeding is carried out by dispersing or flowing a fluid (e.g., cell culture medium) comprising a plurality of cells onto a collagen construct. Alternatively, a collagen construct can be submerged or immersed in a fluid comprising a plurality of cells. In some embodiments of the present invention, the method further comprises removing the fluid and adding a second fluid that optionally comprises cells.

Figure 12A:
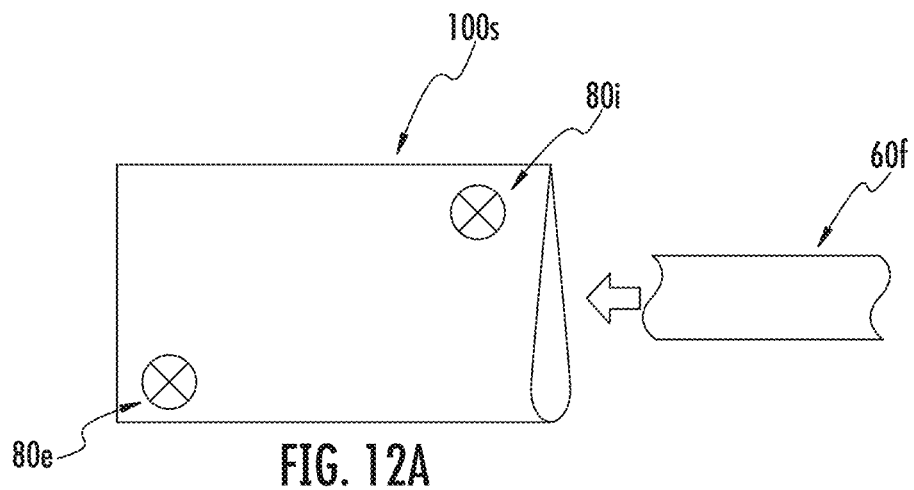
FIGS. 12A-12C are a schematic illustration of a series of steps that can be carried out to prepare an implantable collagen device according to embodiments of the invention.
Figure 12B:
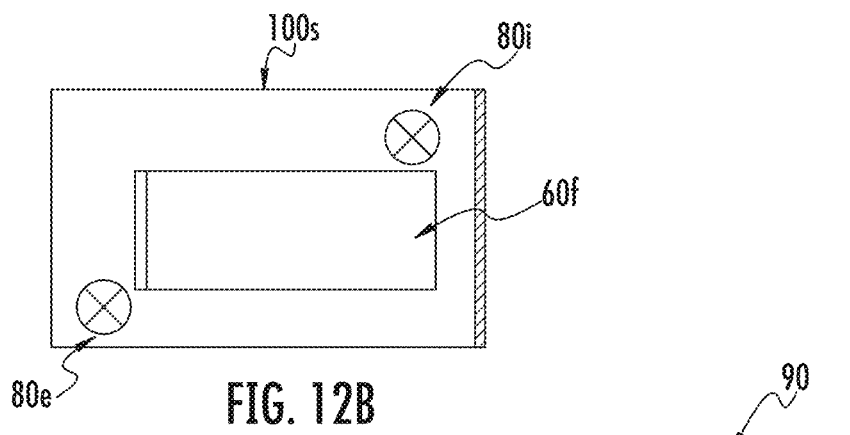
Figure 12C:
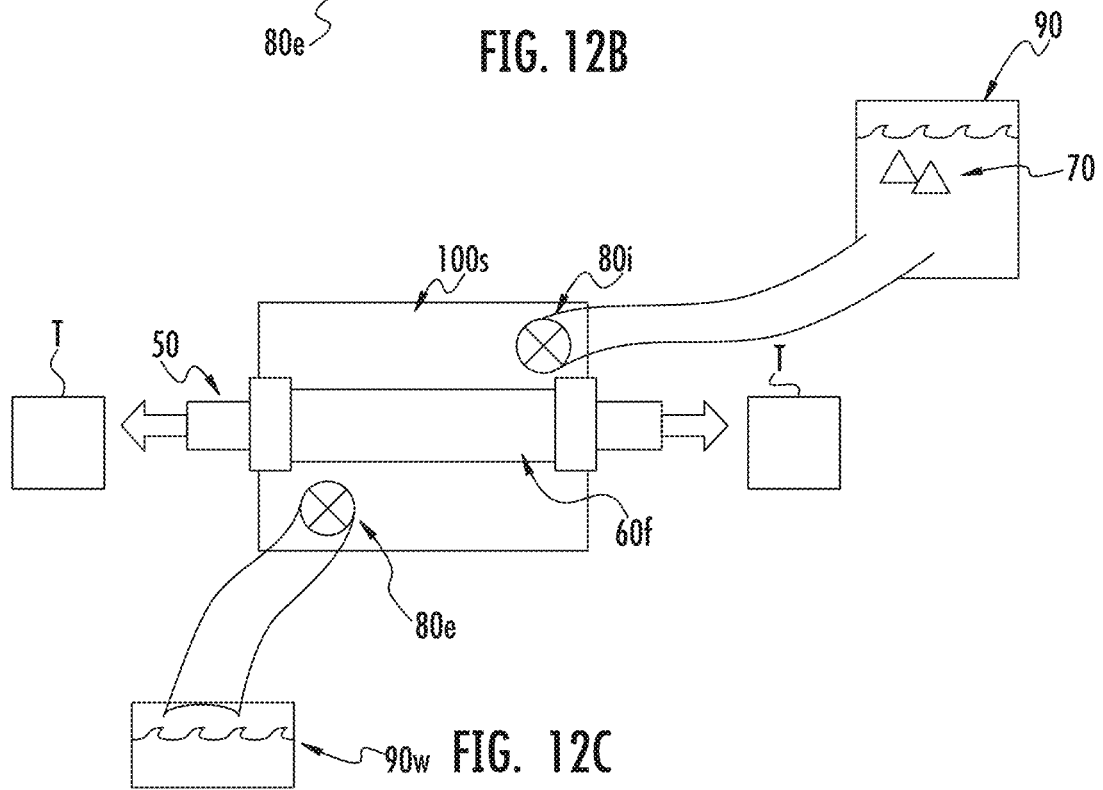

As shown in FIGS. 12A-C, a method of making an implantable collagen fiber construct can comprise: placing at least one elongate collagen fiber 60f in a sealable package 100s having a fluid inlet port 80i and a fluid exit port 80e and then holding the at least one elongate collagen fiber 60f in a defined orientation in the package 100s. Next, a fluid 90 comprising a plurality of cells 70 can be flowed into the fluid inlet port 80i of the package 100s to seed the at least one elongate collagen fiber 60f and then a strain and/or stress can be applied to the at least one elongate collagen fiber 60f. The sealable package 100s can cooperate with a holding member 50 that can attach to the collagen fiber 60f contained within the package 100s and the holding member 50 can attach to a tensioner device T that provides strain and/or stress to a collagen fiber 60f and/or the cells 70. After a certain period of time waste fluid 90w can be collected from the fluid exit port 80e and more fluid 90 can be added via the fluid inlet port 80i.

Figure 13A:
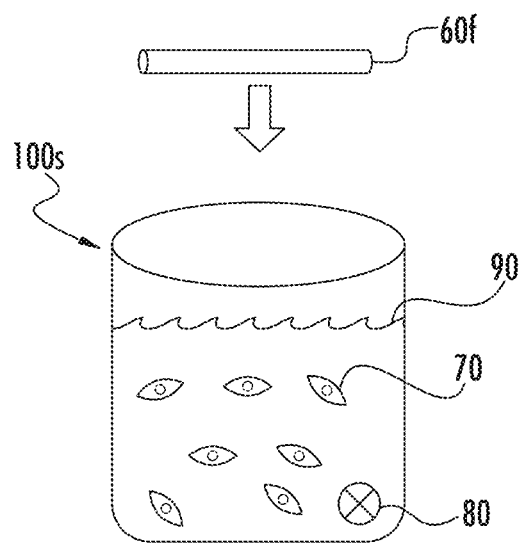
FIGS. 13A-13C are a schematic illustration of a series of steps that can be carried out to prepare an implantable collagen device according to embodiments of the invention.
Figure 13B:
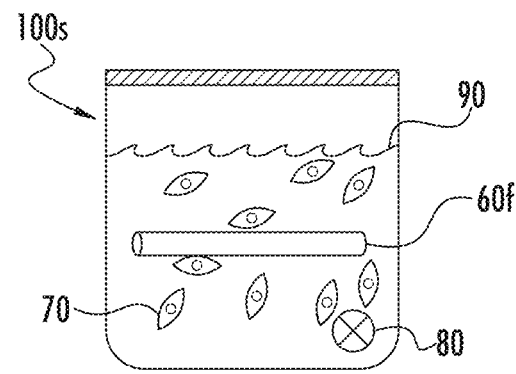
Figure 13C:
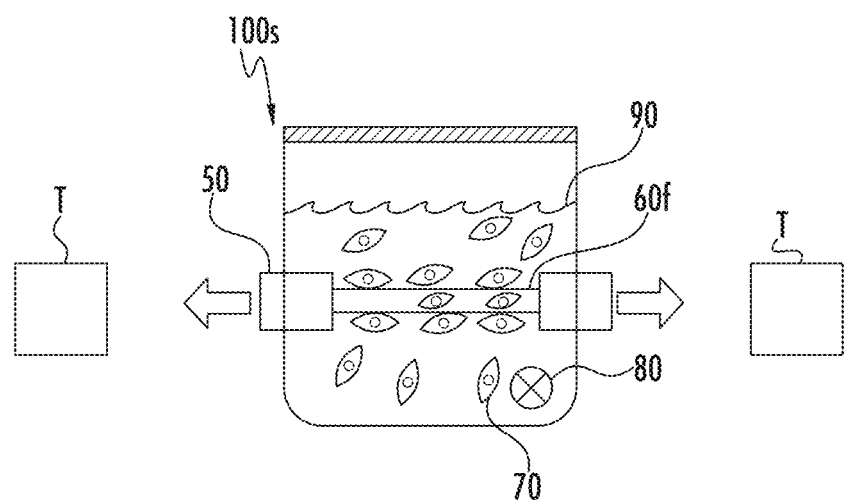

In certain embodiments of the present invention, prior to placing a collagen construct in a sealable package, a fluid optionally comprising one or more cells can be present in the package. After the construct is placed in the package, a strain and/or stress can be applied to the construct and/or cells. As shown in FIGS. 13A-C, a method of making an implantable collagen fiber construct can comprise: placing at least one elongate collagen fiber 60f in a sealable package 100s having a fluid port 80, wherein the sealable package 100s comprises a fluid 90 comprising a plurality of cells 70 (FIG. 13A). Then, closing, typically sealing the package 100s and optionally holding the at least one elongate collagen fiber 60f in a defined orientation in the package 100s (FIG. 13B). The sealable package 100s can cooperate with a holding member 50 that can attach to the collagen fiber 60f contained within the package 100s and the holding member 50 can attach to a tensioner device T that can provide strain and/or stress to a collagen fiber 60f and/or the cells 70. Thus, a strain and/or stress can be applied to the collagen fiber 60f by attaching the holding member 50 to the collagen fiber 60f and applying a strain and/or stress using the tensioner device T (FIG. 13C). The fluid 90 can be drained via the fluid port 80 and a second fluid optionally comprising cells 70 can be added via the fluid port 80.

According to some embodiments of the present invention, upon placing a collagen construct 60 (e.g., at least one elongate collagen fiber 60f) in a sealable package, the elongate collagen fiber can be modified physically (e.g., braided, molded, twisted, etc.) and/or chemically (e.g., changing the chemical composition and/or oxidation state of the collagen construct and/or adding agents or compounds to the collagen construct such as, but not limited to, compounds that aid with cell adhesion to the collagen construct). In some embodiments of the present invention, the collagen construct 60 and/or fiber(s) 60f is subjected to tension after being placed in the sealable package and prior to seeding. The strain and/or stress can be applied after seeding (e.g., after sufficient cell attachment).

In some embodiments of the present invention, the addition and/or removal of a fluid from the package, such as during and/or after seeding, can be done to minimize perturbation of the collagen construct and any attached cells. Removal of a fluid can include removing all or a portion of the fluid. In particular embodiments of the present invention, the fluid can be removed and/or changed after a desired period of time (e.g., about every 12 hours, 24 hours, 2 days, etc.) and replaced with a second fluid, which can optionally comprise one or more cells.

The amount of a fluid added to and/or maintained in the package is generally an amount sufficient to cover or submerge all surfaces of the collagen construct (and/or collagen fiber(s)), while keeping the fluid level to a minimum to prevent slowing of the oxygen diffusion rate to the cells. Alternatively, high levels of a fluid can be maintained in a package for a desired period of time to provide a higher hydrostatic pressure to the cells and/or to slow the oxygen diffusion rate to the cells. As the cells multiply and/or form two dimensional and/or three dimensional structures, the amount of fluid required in the package to cover a collagen construct may increase. Further, the composition of a fluid in the methods of the present invention can be the same or change during the methods of the present invention. In some embodiments of the present invention, a fluid is constantly being refreshed by continually adding and removing a portion of the fluid. During the addition and/or removal of a fluid from the package, a strain and/or stress may or may not be applied.

A further aspect of the present invention comprises a medical kit. A medical kit of the present invention can comprise, consist essentially of, or consist of a package holding an implantable medical device of the present invention in finished or final form for use or in an unfinished or pre-final form. In particular embodiments of the present invention, a medical kit comprises an implantable medical device comprising a plurality of cells attached to a collagen construct, and wherein the cells have organized into a tissue induced by strain and/or stress applied to the collagen construct. The tissue can extend around and through the collagen construct. As shown in FIGS. 6A and 6B, an implantable medical device comprises a tissue 175 of tendon and/or ligament phenotype cells and an extracellular matrix of collagen extends about one or more collagen fibers 60f. In other embodiments of the present invention, a medical kit comprises a package holding an implantable medical device comprising a plurality of cells attached to a collagen construct, wherein one or more cells may or may not have attached to the collagen construct and have not yet formed a tissue.

A medical kit of the present invention can comprise one or more implantable medical devices. A medical kit of the present invention can allow for strain and/or stress to be applied continuously or intermittently until or a time before implantation of the collagen construct. The strain and/or stress can be used to induce a certain cellular event and/or for maintenance of the implantable medical device. A maintenance strain and/or stress can be the same as or different than the strain and/or stress used to form and/or prepare the implantable medical device.

Figure 15A:
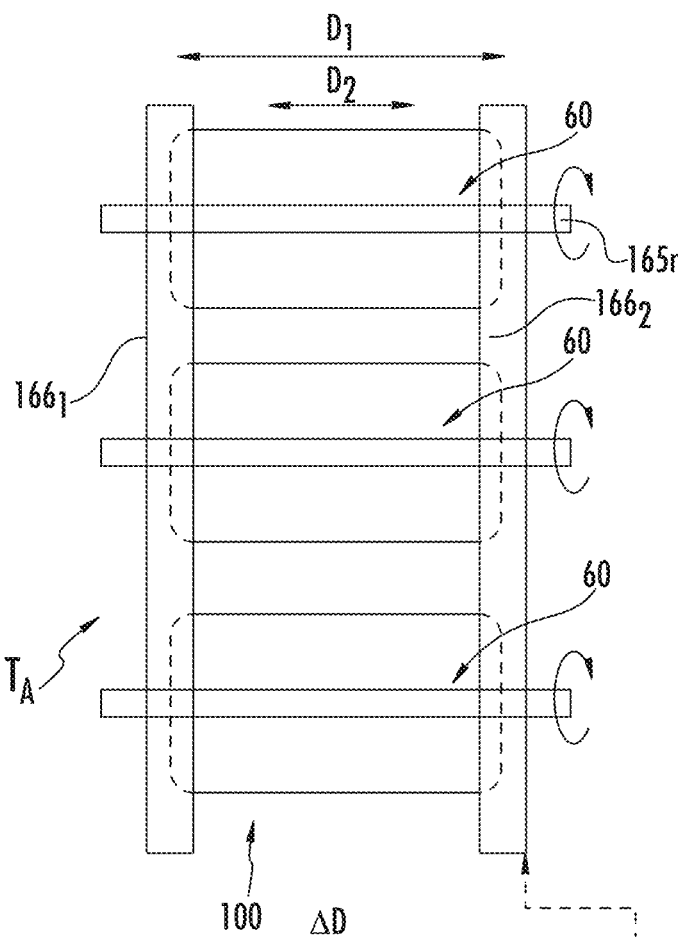
FIG. 15A is a top view of a cyclic autotensioner according to embodiments of the invention.
Figure 15B:
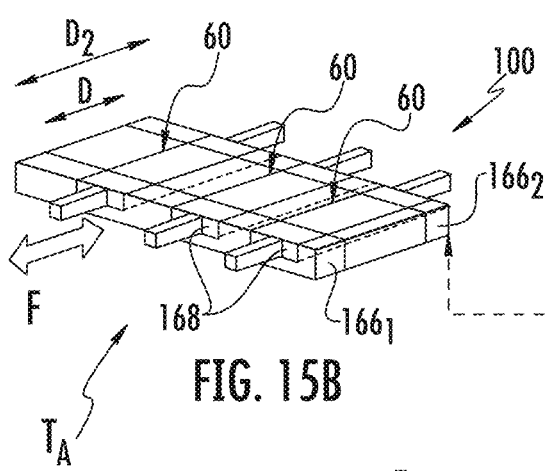
FIG. 15B is a side perspective view of an alternate embodiment of a cyclic autotensioner according to embodiments of the invention.

In certain embodiments of the present invention, a medical kit comprises a portable cyclic autotensioner $T_A$ that can be used to apply strain and/or stress to one or more implantable medical device(s) via attachment to the collagen construct(s) in their respective package(s) (FIG. 15). An autotensioner $T_A$ can be used to prepare an implantable collagen device and/or to maintain an implantable collagen device such as during delivery or storage until implantation of the device. The manual strain and/or stress can be applied to the one or more collagen constructs via a rotational tensile strain and/or stress applied by a rotational mechanism (FIG. 15A) or via a sliding mechanism used to apply the tensile strain and/or stress (FIG. 15B).

Figure 15C:
FIG. 15C is a schematic illustration of medical kit comprising an electric motor according to embodiments of the invention.

As shown in FIG. 15A, an autotensioner $T_A$ holds a plurality of packages 100 with the respective collagen constructs 60. Threaded rods 165r can retract or extend rails 166. The autotensioner $T_A$ can be used to maintain cell differentiation and/or cell viability during storage and/or shipment. The autotensioner $T_A$ can hold one or more packages, such as 2, 3, 4, 5, or more packages. As shown in FIG. 15B, an autotensioner $T_A$ comprises a plurality of linear slides 168 in channels 168c on rails $166_1$ and $166_2$ and holds a package 100 with the collagen constructs 60 or a plurality of separate packages with the respective collagen constructs 60. The linear slides 168 can allow a smaller cyclic strain and/or stress stroke cycle. As shown in FIG. 15C, an electric motor can be connected to the one or more packages 100 to direct the movement of an implantable medical device in an autotensioner $T_A$ and can comprise a processor to provide the time and distance to the electric motor.

In certain embodiments of the present invention, a medical kit comprises one or more fluids that can be utilized to maintain a cell and/or tissue. A medical kit of the present invention can provide an environment suitable for storage of a cell and/or tissue until implantation, such as, but not limited to, providing a contained environment with a desired level of carbon dioxide.

Figure 16:
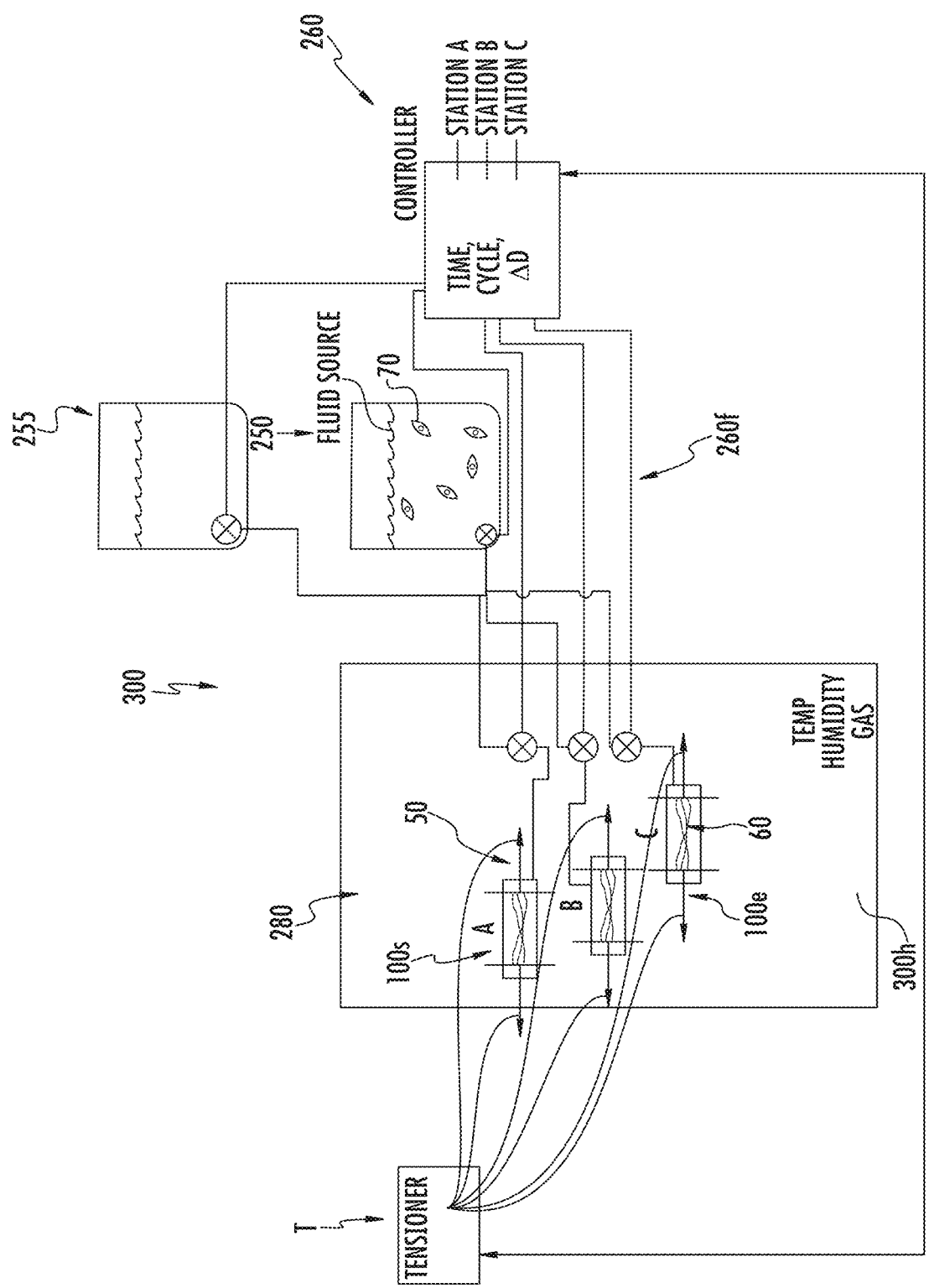
FIG. 16 is a schematic illustration of a system that can provide flow-through fluid while seeding and/or culturing multiple discrete collagen fibers or collagen fiber constructs according to embodiments of the present invention.

Another aspect of the present invention comprises a mass production system with a plurality of packages 100 horizontally and/or vertically stacked for applying strain and/or stress to a plurality of sealable packages holding one or more collagen constructs 60. As shown in FIG. 16, a system 300 for applying a tensile strain and/or stress to a plurality of sealable packages 100s holding collagen constructs 60 can comprise a plurality of cooperating holding members 50 attached to opposing end portions of a plurality of the packages 100e enclosing respective collagen constructs 60; at least one fluid source 250 in communication with the packages 100s, the fluid source 250 comprising cells 70; and at least one tensioner T with an automated stroke cycle in communication with the holding members.

The tensioner T can include or be in communication with a controller 260 that allows a user to select the stroke cycle to apply to the collagen constructs 60.

In certain embodiments of the present invention, the system comprises at least two fluid sources, wherein the first fluid source 250 comprises cells 70 and is used to seed to the collagen constructs 60 and the second fluid source 255 comprises a fluid that does not contain cells. The second fluid source 260 can replace the first fluid source 250 after a desired period of time (e.g., 12 hours, 24 hours, 2 days, etc.). In some embodiments of the present invention, the first and second fluid sources alternate in supplying fluid to the collagen constructs. A shared fluid path can be used to deliver both fluids to respective stations/vessels held thereat as shown. Dedicated ports and paths may also be used (not shown).

In other embodiments of the present invention, the system comprises an incubator 280 with a housing 300h that encloses the pouches. An incubator can maintain and/or control the environment the packages are exposed to. In some embodiments of the present invention, an incubator maintains/controls the temperature, humidity levels, and/or atmosphere (i.e., pressure and gas content, such as carbon dioxide percentage) the packages are exposed to.

The system can include a flow control system 260f in communication with the at least one fluid source and the controller 260. The flow control system can include, for example, valves, pumps and/or other flow control members. The controller 260 can control operation of the flow control system to selectively (automatically) direct when to flow fluid from the first fluid source to one or more of the pouches.

Embodiments of the invention will now be explained with respect to the following non-limiting examples.

EXAMPLES

Example 1

A plurality of elongate collagen fibers can be braided to form a braided collagen fiber construct while the fibers are held at a tension $t_n$. The braided collagen fiber construct can be placed in a sealable, flexible bag and secured in a defined orientation in the bag. The bag can then be sealed (except for one or more ports where used) and connected to an automated tensioner via a set of cooperating holding members, which can hold the opposing ends of the bag. Once connected, the tensioner can be manually or automatically set to apply a static tensile load to the collagen construct that is substantially if not totally the same as the tension $t_{f1}$ used to braid the collagen fibers.

A cell culture medium containing human mesenchymal stems cells and/or fibroblasts can be added to the bag before, after or during the placement of the collagen fiber construct in the bag. In some embodiments, the cell culture medium can be flowed into the bag using a port and defined flow path from a culture source. The cell culture medium can be added until there is a sufficient quantity to cover all surfaces of the braided collagen fiber construct with the medium. The quantity can be such that a volume of the medium in the bag is held to a minimum to minimize slowing of the rate of oxygen diffusion to the cells. After the addition of the cells, the bag can be kept under standard cell culture conditions. The static tensile load $t_{f1}$ can be maintained via the tensioner for about 24 hours or until a majority of the cells have attached to the braided collagen fiber construct.

After approximately 24 hours or after a majority of the cells have attached to the braided collagen fiber construct, a cyclic tensile load of about 5% to about 10% strain of $t_{C1}$, which is greater than or equal to $t_{f1}$, at about 1 to about 4 Hz can be applied to the braided collagen fiber construct for about thirty minutes each day for about 4 days to about 2 weeks. For the remainder of the day, no tension or stress/strain can be applied to the braided collagen fiber construct.

Example 2

A plurality of elongate collagen fibers can be braided to form a braided collagen fiber construct or woven to form a woven collagen fiber construct, while the fibers are held at a tension $t_{f2}$. The woven or braided collagen fiber construct can be placed in a sealable, flexible bag, which contains cell culture medium and human mesenchymal stems cells and/or fibroblasts. The woven or braided collagen fiber construct can be secured in a defined orientation in the bag and the bag can be sealed. The bag can be kept under standard cell culture conditions. No tension or a light tension (which does not apply more than a di minimis stress or strain) can be applied to the braided collagen fiber construct for between about 12 to about 24 hours.

After sufficient cell attachment, the tensioner can be set to apply a cyclic tensile load to the braided collagen fiber construct of about 1% to about 5% strain of $t_{C2}$, which is greater than or equal to $t_{f2}$, at about 1 to about 2 Hz for about 2 hours each day for about 4 days to about 2 weeks. For the remainder of the day during this timeframe, a static tensile load of about 1% of $t_{f2}$ can be applied to the braided collagen fiber construct.

Example 3

An elongate collagen fiber construct can be formed under a tensile strain and/or stress $t_{f3}$ and once formed can remain under tensile strain and/or stress $t_{f3}$. The collagen fiber construct can be placed in a clean, typically sterile, flexible bag with inlet and exit ports and secured in a defined orientation in the bag. The bag can be sealed (with one or more optional intake and/or fluid exit ports) and/or connected to flow paths of fluid sources and connected to a tensioner via a set of cooperating holding members, which can hold the opposing ends of the bag.

Cell culture medium containing human mesenchymal stems cells and/or fibroblasts can be added to the bag until all surfaces of the collagen fiber construct are covered with the medium. The bag can then be packaged with the tensioner comprising or in communication with a controller, which can be set to maintain the tensile strain and/or stress $t_{f3}$ for about 4 hours, then apply a cyclic tensile strain and/or stress at about 5% strain of $t_{C3}$, which is less than or equal to $t_{f3}$, at 1 Hz for about 1 hour each day for about 1 month. For the remainder of the day during this period, the tensile strain and/or stress $t_{f3}$ can be resumed.

The bag can also be packaged with a fluid source connected via the inlet port and the controller can be set to remove the fluid every 24 hours via the exit port and add new fluid comprising cell culture medium via the inlet port. The bag with the tensioner and fluid source can then be shipped to a facility for implantation in a subject. The inlet and outlet ports can be combined as a single port or more than two ports.

Example 4

An elongate collagen fiber construct can be formed under a tensile strain and/or stress $t_{f4}$ and once formed can remain under tensile strain and/or stress $t_{f4}$. The collagen fiber construct can then be placed in a sealable, flexible bag with inlet and exit ports and secured in a defined orientation in the bag. Next, the bag can be sealed and connected to a tensioner via a set of cooperating holding members, which cab hold the opposing ends of the bag.

Cell culture medium containing human mesenchymal stems cells and/or fibroblasts can be added to the bag until all surfaces of the collagen fiber construct are covered with the medium. The tensile load $t_{f4}$ can be maintained via the tensioner for about 24 hours. After approximately 24 hours, a cyclic tensile load of between about 4% to about 8% strain of $t_{C4}$, which is greater than or equal to $t_{f4}$, at about 0.5 to about 2 Hz can be applied to the collagen fiber construct for about 1 hour each day for about 2 weeks or until a three dimensional cell structure is formed. For the remainder of the day, a very low, but typically no, strain/stress may be applied to the collagen fiber construct.

At about 2 weeks or once a three dimensional cell structure is formed, the bag can be packaged with the tensioner comprising a controller, which can be set to maintain the same strain and/or stress protocol described above for about 1 week or until implantation in a subject. The bag can also be packaged with a fluid source comprising cell culture medium connected via the inlet port and the controller can be set to remove the fluid every 24 hours via the exit port and add new fluid via the inlet port. The bag with an on-board tensioner (forming part of a shipment container) and fluid source can then be shipped to a facility for implantation in a subject.

Example 5

A construct formed with elongate collagen fibers can be placed in a defined orientation in a container, such as, but not limited to, a cell culture vessel or a sterile, flexible bag or pouch. Cell culture medium containing stems cells and/or fibroblasts can be added to the container until surfaces of the collagen fiber construct are covered with the medium.

Holding members of an automated tensioner, such as clamps or other holding member configurations, can attach to each opposing end of the bag/construct. The holding members can be moved to pull the construct axially to remove slack. An inter-clamp distance can be measured or defined and an initial offset strain of about 1% is applied. Cyclic strain can then be applied. The magnitude of strain can vary between 2% and 15%. The construct can substantially always be held under tension going from the initial offset to the desired cyclic strain. The cyclic tension can go from 1% to about 15% above the initial strain at a defined frequency.

The cyclic tension and/strain continue until at least one of the following outcomes occurs: (i) the construct is populated by ligament/tendon phenotype cells only, cells that have been 'differentiated' into tendon/ligament phenotype cells; or (ii) the construct has the phenotype cells and an extracellular matrix that is predominantly collagen.

The amount of phenotype cells and extracellular matrix can increase thickness of the construct by between 10-200%, e.g., the thickness can double.

The phenotype cells, extracellular matrix or tissue of same can reside between the points of contact of the holders (e.g., clamps) or over at least 50% of the length of the construct. For example, over at least 50% of a length of the construct the thickness or height of organized cells/tissue can increase a thickness of the construct by between 50-200%, e.g., the cells double the thickness fiber construct itself as cells grow and organize and produce a tendon-like tissue.

Example 6

A construct formed with woven elongate collagen fibers can be placed in a defined orientation in a container, such as, but not limited to, a cell culture vessel or a sterile, flexible bag or pouch. The construct can simulate elastic modulus of a natural tendon for tendon replacement or repair. Cell culture medium containing stems cells and/or fibroblasts can be added to the container to contact the collagen fibers. Cyclic strain can then be applied to the fibers. Because the construct mimics a natural tendon, it imparts proper strain to promote and cellular changes into tendon phenotype cells such that the cells from the cell culture change into tenocyte morphology to have elongated cells aligned with the axial direction of the fibers or fibrils.

The magnitude of strain can vary between 2% and 15%. The construct can substantially always be held under tension going from the initial offset to the desired cyclic strain. The cyclic tension can go from 1% to about 15% above the initial strain at a defined frequency.

The cyclic tension and/strain continue until at least one of the following outcomes occurs: (i) the construct is populated by target phenotype cells only, cells that have been 'differentiated' into target tissue phenotype cells; or (ii) the construct has the phenotype cells and an extracellular matrix that is predominantly collagen.

The amount of phenotype cells and extracellular matrix can increase thickness of the construct by between 10-200%, e.g., the thickness can double.

For example, over at least 50% of a length of the construct the thickness or height of organized cells/tissue can increase a thickness of the construct by between 50-200%, e.g., the cells double the thickness fiber construct itself.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A medical kit, comprising:
a single-use flexible package holding a collagen construct comprising a plurality of synthetic elongate collagen fibers, wherein the plurality of synthetic elongate collagen fibers comprise ligament or tendon phenotype cells, and wherein the tendon or ligament phenotype cells extend over at least 50% of a length of the collagen fibers.

2. The medical kit claim 1, wherein the plurality of synthetic elongate collagen fibers are cross-linked with NDGA, and wherein the tendon or ligament phenotype cells cover at least a major portion of a surface area of each of the synthetic elongate collagen fibers for at least 50% of the length of the plurality of synthetic elongate collagen fibers.

3. The medical kit of claim 1, wherein the plurality of synthetic elongate collagen fibers are wound, braided, twisted and/or woven together.

4. The medical kit of claim 1, wherein the collagen construct is a tendon or ligament prosthesis and has a tensile strength, stiffness, and dynamic flexibility that meets or exceeds that of a natural tissue the collagen construct is designed to mimic.

5. The medical kit of claim 1, wherein the cells are differentiated cells derived from cells selected from the group consisting of embryonic, neonatal or adult cells, pluripotent stem cells, mesenchymal stem cells, tendon and/or ligament fibroblasts, or combinations thereof.

6. The medical kit of claim 1, wherein the plurality of elongate collagen fibers include the tendon phenotype cells and at least 20% extracellular matrix of collagen by volume, dry.

7. The medical kit of claim 1, wherein the plurality of synthetic elongate collagen fibers are derived from soluble collagen and define a construct body with a shape as the collagen construct, and wherein the construct body includes the tendon or the ligament phenotype cells and an extracellular matrix of collagen, in an amount between about 20% to 200% by volume of the construct body, dry.

8. A medical kit, comprising:
a single-use flexible package holding a collagen construct comprising a plurality of elongate collagen fibers, wherein the elongate collagen fibers comprise ligament or tendon phenotype cells, and wherein the tendon or ligament phenotype cells extend over at least 50% of a length of the collagen fibers,
wherein the elongate collagen fibers of the construct further comprise an extracellular matrix comprising collagen, and wherein collagen is present in the extracellular matrix in an amount greater than other extracellular matrix proteins.

9. The medical kit of claim 8, wherein the plurality of elongate collagen fibers is between 2-1000.

10. The medical kit of claim 8, wherein the plurality of elongate collagen fibers are arranged as a construct body providing the collagen construct, and wherein the attached tendon or ligament phenotype cells and extracellular matrix comprising collagen are organized into tendon-like or ligament-like tissue that increases a volume of the construct body, measured dry, by between about 20-200%, or that increases a thickness of the construct body by between 10%-200%.

11. A medical kit, comprising:
a single-use flexible package holding a collagen construct comprising a plurality of elongate collagen fibers, wherein the elongate collagen fibers comprise ligament or tendon phenotype cells, and wherein the tendon or ligament phenotype cells extend over at least 50% of a length of the collagen fibers, wherein the flexible package is or comprises a polymeric pouch, the kit further comprising an auto-tensioner releasably attached to the pouch to apply a maintenance strain and/or stress to the collagen construct.

* * * * *

UNITED STATES PATENT AND TRADEMARK OFFICE
CERTIFICATE OF CORRECTION

PATENT NO. : 10,689,621 B2  
APPLICATION NO. : 15/843695  
DATED : June 23, 2020  
INVENTOR(S) : Thomas J. Koob Page 1 of 1

It is certified that error appears in the above-identified patent and that said Letters Patent is hereby corrected as shown below:

In the Specification

Column 7, Line 52: Please correct "off 5%" to read -- of $\pm 5\%$ --

Column 24, Line 61: Please correct "$t_n$" to read -- $t_{f1}$ --

Signed and Sealed this  
Seventeenth Day of November, 2020

Andrei Iancu  
*Director of the United States Patent and Trademark Office*